United States Patent [19]

Grammenos et al.

[11] Patent Number: 5,602,181
[45] Date of Patent: Feb. 11, 1997

[54] NAPHTHYL ETHERS, THEIR PREPARATION, COMPOSITIONS CONTAINING THEM AND THEIR USE

[75] Inventors: Wassilios Grammenos, Ludwigshafen; Reinhard Kirstgen, Neustadt; Hartmann König, Limburgerhof; Klaus Oberdorf, Heidelberg; Hubert Sauter, Mannheim; Gisela Lorenz, Neustadt; Eberhard Ammermann, Heppenheim, all of Germany

[73] Assignee: BASF Aktiengesellschaft, Ludwigshafen, Germany

[21] Appl. No.: 321,770

[22] Filed: Oct. 12, 1994

[30] Foreign Application Priority Data

Oct. 12, 1993 [DE] Germany .................. 43 34 709.6

[51] Int. Cl.⁶ .................. C07C 321/28; C07C 233/09
[52] U.S. Cl. .................. 514/618; 514/619; 514/510; 514/269; 564/162; 564/165; 564/167; 564/172; 544/319; 544/314; 544/408; 544/312; 544/316; 544/219; 544/182; 548/142; 548/144; 548/132; 548/226; 548/229; 548/183; 548/182; 548/301
[58] Field of Search .................. 564/165, 162; 514/619, 618

[56] References Cited

U.S. PATENT DOCUMENTS

| | | |
|---|---|---|
| 4,999,042 | 3/1991 | Anthony et al. .................. 71/88 |
| 5,057,537 | 10/1991 | Wenderoth et al. .................. 514/510 |
| 5,334,607 | 8/1994 | Sauter et al. .................. 514/378 |

FOREIGN PATENT DOCUMENTS

| | | |
|---|---|---|
| 0044448 | 1/1982 | European Pat. Off. . |
| 0254426 | 1/1988 | European Pat. Off. . |
| 0253213 | 1/1988 | European Pat. Off. . |
| 0374811 | 6/1990 | European Pat. Off. . |
| 0385357 | 9/1990 | European Pat. Off. . |
| 0468684 | 1/1992 | European Pat. Off. . |
| 0513580 | 11/1992 | European Pat. Off. . |
| 0546387 | 6/1993 | European Pat. Off. . |

*Primary Examiner*—Mukund J. Shah
*Assistant Examiner*—King Lit Wong
*Attorney, Agent, or Firm*—Oblon, Spivak, McClelland, Maier & Neustadt, P.C.

[57] ABSTRACT

Naphthyl ethers of the general formula I

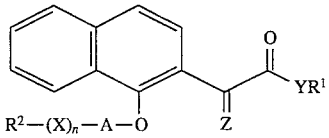

where the index and the substituents have the meanings defined in the specification.

11 Claims, No Drawings

NAPHTHYL ETHERS, THEIR PREPARATION, COMPOSITIONS CONTAINING THEM AND THEIR USE

The present invention relates to naphthyl ethers of the general formula I

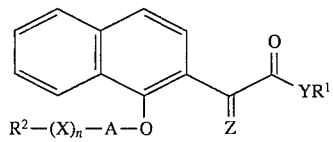

where the index and the substituents have the following meanings:

A is unsubstituted or substituted phenyl or unsubstituted or substituted 5- to 6-membered heteroaryl, which in addition to carbon ring members can contain one to three nitrogen atoms or one or two nitrogen atoms and an oxygen or sulfur atom or an oxygen or sulfur atom as further ring members;

n is 0 or 1;

X is oxygen, sulfur or nitrogen, the nitrogen atom carrying one of the following radicals: hydrogen, $C_1$–$C_4$-alkyl, $C_1$–$C_4$-alkoxy, $C_3$–$C_6$-cycloalkyl, unsubstituted or substituted phenyl or unsubstituted or substituted benzyl;

Y is oxygen or for the case where Z is $NOCH_3$: oxygen or nitrogen, the nitrogen atom carrying one of the following radicals: hydrogen, $C_1$–$C_4$-alkyl or $C_1$–$C_4$-alkoxy; Z is $CHOCH_3$, $NOCH_3$, $CHCH_3$ or $CHCH_2CH_3$;

$R^1$ is $C_1$–$C_4$-alkyl;

$R^2$ is unsubstituted or substituted $C_1$–$C_6$-alkyl, $C_3$–$C_6$-cycloalkyl, $C_2$–$C_6$-alkenyl or $C_3$–$C_6$-alkynyl; unsubstituted or substituted phenyl;

unsubstituted or substituted 5- or 6-membered heteroaryl, containing in addition to carbon ring members one to three nitrogen atoms or one or two nitrogen atoms and an oxygen or sulfur atom as further ring members;

or for the case where the value of n is 0, additionally to the above meanings: halogen, $C_1$–$C_6$-alkoxy, $C_1$–$C_4$-alkylsulfoxyl or phenylsulfoxyl, the phenyl ring in turn being able to carry substituents.

The literature (EP-A 385 357) discloses naphthyl ethers containing an aryloxy-, arylthio- or arylalkoxyalkyl ether function as fungicides.

It is an object of the present invention to provide novel naphthyl ethers having an improved and widened spectrum of action.

We have found that this object is achieved by the naphthyl ethers I defined at the outset. We have additionally found processes for the preparation of the naphthyl ethers I, compositions containing them and their use for the control of animal pests or harmful fungi.

The compounds according to the invention are accessible in various ways known from the literature in a similar manner. Starting from 1-naphthol (II), the compounds I where Y is oxygen are obtained, preferably according to one of the processes compiled in the following reaction scheme:

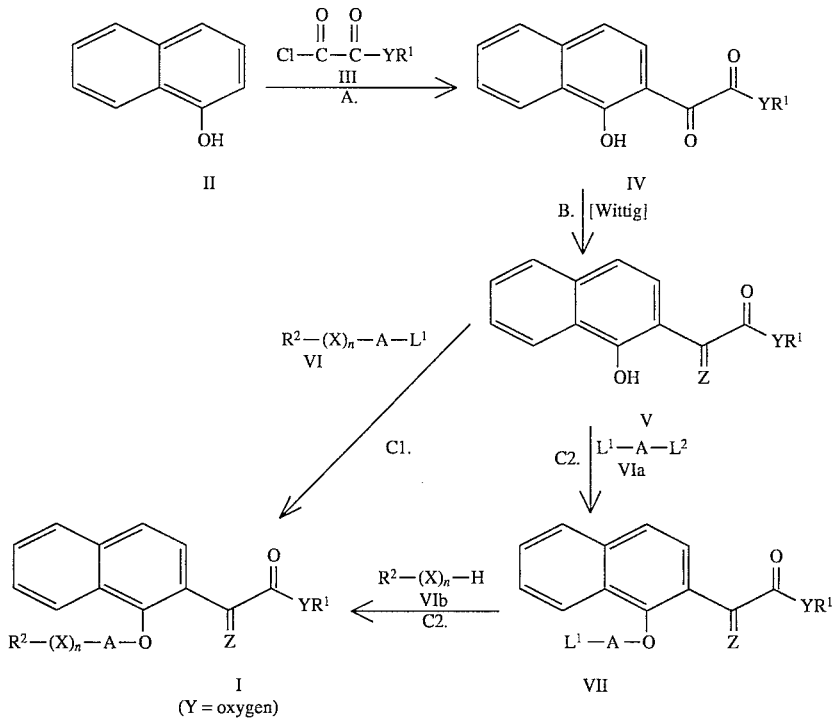

(Y=oxygen)

The synthesis of the compounds I where Y is oxygen in each case comprises

A) the acylation of the 2-position of the naphthyl ring system (reaction of II with III);

B) introduction of the group Z (reaction of IV to give V); by 1. a Wittig or Wittig-like reaction of the alpha-ketocarbonyl group for compounds I where Z is $CHOCH_3$, $CHCH_3$ or $CHCH_2CH_3$ or 2. reaction with O-methylhydroxylamine or with hydroxylamine and subsequent methylation for compounds I where Z is NOCH₃;

C1) the etherification of the naphthol in one stage (reaction of V to give I) or C2) the etherification of the naphthol in two stages (reaction of V via VII to give I).

The corresponding compounds I, where Y is an unsubstituted or substituted nitrogen atom, are obtained by reaction of compounds V, VII or I, where Y is oxygen, with an appropriate amine.

The reactions are customarily specifically carried out as follows. In the following reaction equations the groups not involved in the reaction concerned are in each case abbreviated by —# (for the 2-position of the naphthyl ring) or —O*, (for the 1-position of the naphthyl ring).

A) The acylation of the 2-position of the naphthyl ring system (reaction of II with III)

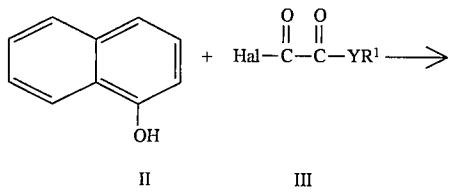

II  III

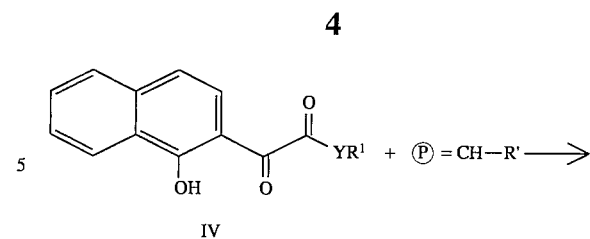

IV

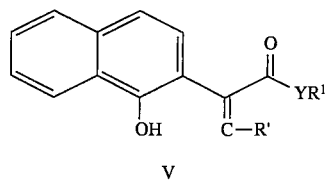

V

{Ⓟ=eg. triphenylphosphorus ylide or dialkoxyphosphonate;

R'=OCH₃, CH₃ or CH₂CH₃}

The reaction of the compounds IV to give the corresponding derivatives V is carried out by Wittig or Wittig-like reaction in a manner known per se (EP-A 44 448; EP-A 385 357).

B.2 Introduction of the group Z (reaction of IV to give V) by reaction with O-methylhydroxylamine or with hydroxylamine and subsequent methylation for compounds I where Z is NOCH₃

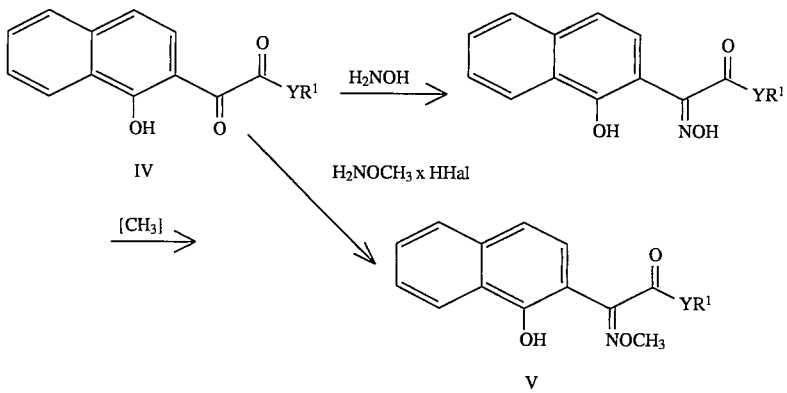

-continued

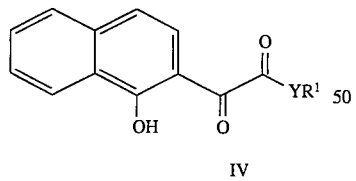

IV

{Hal=halogen, in particular chlorine}

The naphthol II is acylated by reaction with methyl oxalyl halides, in particular the chloride, in a manner known per se (Piccolo et al., Tetrahedron 42, 885 (1986); EP-A 385 357) in an inert organic solvent (eg. dichloroethane) in the presence of a Lewis acid (eg. titanium tetrachloride).

B.1 Introduction of the group Z (reaction of IV to give V) by a Wittig or Wittig-like reaction of the alpha-ketocarbonyl group for compounds I where Z is CHOCH₃, CHCH₃ or CHCH₂CH₃

{[CH₃]=eg. methyl iodide or dimethyl sulfate; Hal= halogen, eg. Cl, Br or I}

The introduction of the group Z=NOCH₃ is carried out by reaction with O-methylhydroxylamine or by reaction with hydroxylamine to give the corresponding oxime and subsequent methylation in a manner known per se (EP-A 253 213; EP-A 385 357).

C1) The etherification of the naphthol in one stage (reaction of V to give I)

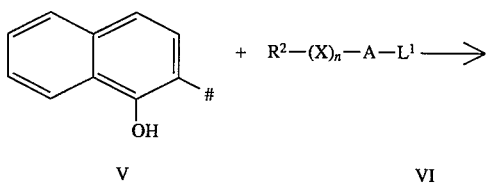

V  VI

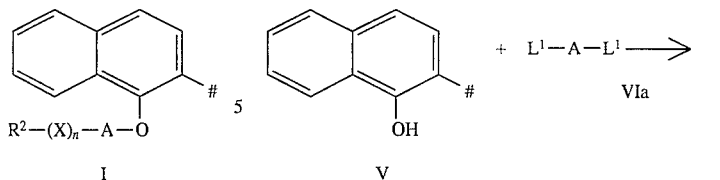

I

{$L^1$ =eg. halogen such as fluorine, chlorine or bromine, or mesylate (methane/sulfonate) or tosylate (4-toluenesulfonate)}

This reaction is customarily carried out at from 0° to 120° C., preferably 20° C. to 80° C.

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol, ketones such as acetone and methyl ethyl ketone as well as dimethyl sulfoxide, dimethylformamide, dimethylacetamide, 1,3-dimethylimidazolidin-2-one and 1,3-dimethyltetrahydro-2(1H)-pyrimidine, particularly preferably acetonitrile, methylene chloride, acetone and dimethylformamide. Mixtures of the solvents mentioned can also be used.

Suitable bases are generally inorganic compounds such as alkali metal and alkaline earth metal hydroxides such as lithium hydroxide, sodium hydroxide, potassium hydroxide, calcium hydroxide, alkali metal and alkaline earth metal alkoxides such as lithium oxide, sodium oxide, calcium oxide and magnesium oxide, alkali metal and alkaline earth metal hydrides such as lithium hydride, sodium hydride, potassium hydride and calcium hydride, alkali metal and alkaline earth metal carbonates such as potassium carbonate and calcium carbonate and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride and also alkali metal and alkaline earth metal alkoxides such as sodium methoxide, sodium ethoxide, potassium methoxide, potassium tert-butoxide and dimethoxymagnesium, additionally organic bases, eg. tertiary amines such as trimethylamine, triethylamine, diisopropylethylamine and N-methylpiperidine, pyridine, substituted pyridines such as collidine, lutidine and 4-dimethylaminopyridine and also bicyclic amines.

Sodium hydroxide, sodium hydride, potassium carbonate and potassium tert-butoxide are particularly preferred.

The bases are in general used in an equimolar amount, in excess or where appropriate as a solvent.

It may be advantageous for the reaction to add a catalytic amount of a crown ether such as eg. 18-crown-6 or 15-crown-5.

The reaction can also be carried out in two-phase systems consisting of a solution of alkali metal or alkaline earth metal hydroxides or alkali metal or alkaline earth metal carbonates in water and an organic phase such as eg. halogenated hydrocarbons. The phase-transfer catalysts employed can be ammonium halides and tetrafluoroborates such as eg. benzyltriethylammonium chloride, benzyltributylammonium bromide, tetrabutylammonium chloride, hexadecyltrimethylammonium bromide or tetrabutylammonium tetrafluoroborate and phosphinium halides such as tetrabutylphosphinium chloride or tetraphenylphosphonium bromide.

C2) The etherification of the naphthol in two stages (reaction of V via VII to give I).

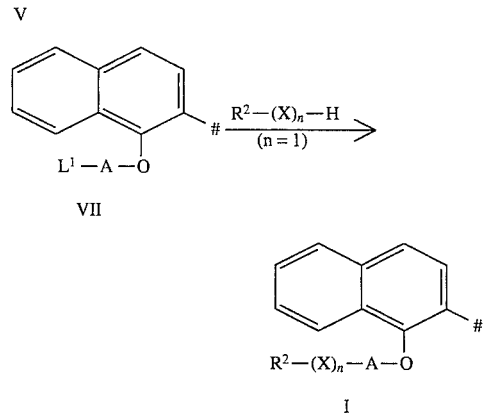

The corresponding compounds I where Y is an unsubstituted or substituted nitrogen atom are obtained by reaction of compounds V, VII or I, where Y is oxygen, with an appropriate amine in a manner known per se (Houben-Weyl, Vol. E5, p. 983ff).

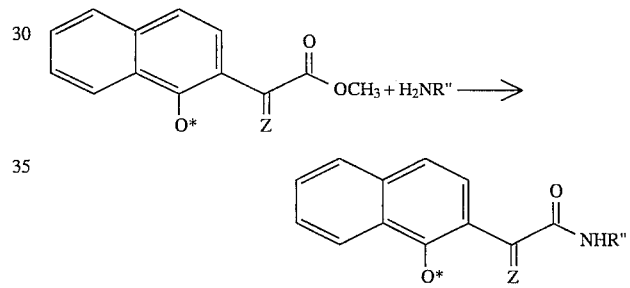

{R"=hydrogen, $C_1$–$C_4$-alkyl or $C_1$–$C_4$-alkoxy}

This reaction is customarily carried out at from 0° C. to 60° C., preferably 10° C. to 40° C.

Methylamine can be metered into a solution of II by gaseous introduction or as an aqueous solution.

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, alcohols such as methanol, ethanol, n-propanol, isopropanol, n-butanol and tert-butanol, particularly preferably methanol, toluene and tetrahydrofuran.

Mixtures of the solvents mentioned can also be used.

With respect to their biological action against animal pests and harmful fungi, compounds of the formula I are suitable where the index and the substituents have the following meanings:

A is unsubstituted or substituted phenyl or unsubstituted or substituted 5- to 6-membered heteroaryl which, in addition to carbon ring members, can contain one to three nitrogen atoms or one or two nitrogen atoms and an oxygen or sulfur atom or an oxygen or sulfur atom as further ring members, eg. unsubstituted or substituted phenyl, furyl, thienyl, pyrrolyl, pyrazolyl, imidazolyl, triazolyl, isoxazolyl, oxazolyl, oxadiazolyl, isothiazolyl, thiazolyl, thiadiazolyl, pyridyl, pyridazinyl, pyrimidyl, pyrazinyl or triazinyl, the bonds to the adjacent groups $(X)_n$ or O preferably taking place via two meta- or pseudo-meta carbon ring members, in particular one of the groups A.1 to A.42
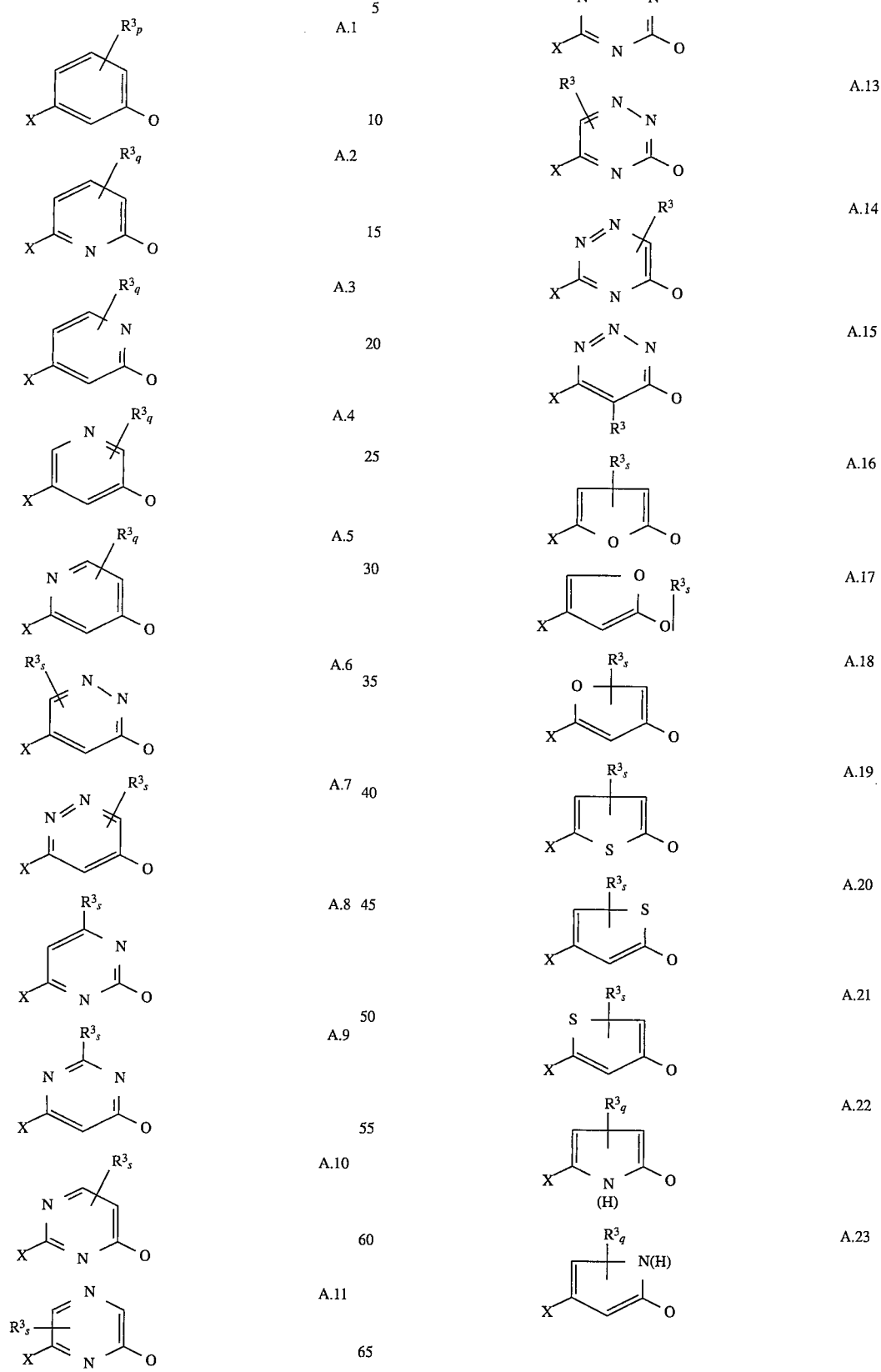

where the symbols x— and —o serve to indicate to which of the radicals adjacent to A the bond is directed, namely the bond designated by x— to the radical —(X)$_n$R$^2$ and the bond designated by —o to the oxygen atom, and where p is 0, 1, 2, 3 or 4, it being possible for the radicals R$^3$ to be different if p>1;

q is 0, 1 or 2 or 3, it being possible for the radicals R$^3$ to be different if q is>1;

s is 0, 1 or 2, it being possible for the radicals R$^3$ to be different if s is>1;

the radicals R$^3$ being bonded to a C atom of the ring or, in the case of the radicals A.22, A.23, A.24, A.33, A.34, A.35 and A.36, additionally to an N atom of the ring and R$^3$ has the following meanings:
hydrogen, halogen, C$_1$–C$_4$-alkyl, C$_1$–C$_4$-haloalkyl, C$_1$–C$_4$-haloalkoxy and C$_3$–C$_6$-cycloalkyl;

n is 0 or 1;

X is oxygen, sulfur or nitrogen, the nitrogen atom carrying one of the following radicals: hydrogen, C$_1$–C$_4$-alkyl, C$_1$–C$_4$-alkoxy, C$_3$–C$_6$-cycloalkyl, phenyl or benzyl, the phenyl ring and the benzyl radical being able to carry one to five halogen atoms or one to three of the following radicals: halogen, C$_1$–C$_4$-alkyl, C$_1$–C$_4$-haloalkyl, C$_1$–C$_4$-alkoxy, C$_1$–C$_4$-haloalkoxy, C$_3$–C$_6$-cycloalkyl, phenyl or benzyl;

Y is oxygen, a direct bond or for the case where Z is NOCH$_3$: oxygen, a direct bond or nitrogen, the nitrogen atom carrying one of the following radicals: hydrogen, C$_1$–C$_4$-alkyl or C$_1$–C$_4$-alkoxy;

Z is CHOCH$_3$, NOCH$_3$, CHCH$_3$ or CHCH$_2$CH$_3$;

R$^1$ is C$_1$–C$_4$-alkyl;

R$^2$ is C$_1$–C$_6$-alkyl, C$_3$–C$_6$-cycloalkyl, C$_2$–C$_6$-alkenyl or C$_3$–C$_6$-alkynyl, it being possible for these groups to be partly or completely halogenated and/or to carry one or two of the following radicals:
hydroxyl,
cyano, isocyano,
nitro,
formyl,
amino,
formylamino,
carboxyl,
sulfoxyl,
carbonylamino,
alkylamino,
dialkylamino,
alkylcarbonyl,
alkoxycarbonyl,
alkylaminocarbonyl,
alkylsulfonyl or
phenylsulfonyl;
phenyl, which can carry one to five halogen atoms and/or one to three of the following radicals:
amino (—$NH_2$),
carboxyl (—$CO_2H$),
carbonylamino (—$CONH_2$),
cyano (—CN),
formyl (—CHO),
formylamino (—NHCHO),
hydroxyl (—OH),
isocyano (—NC),
nitro (—$NO_2$),
sulfoxyl (—$SO_3H$),
thiocarboxamido (—NHCOSH),
thiocyanato (—NCS),
alkyl,
haloalkyl,
alkylcarbonyl,
alkylcarbonyloxy,
alkylcarbonylthio,
alkylcarbonylamino,
alkylsufonyl,
alkylsulfonyloxy,
alkylsulfonylamino,
alkoxy,
haloalkoxy,
alkoxycarbonyl,
alkoxyiminoalkyl,
alkylthio,
alkylthiocarbonyl,
alkylamino,
alkylaminocarbonyl,
dialkylamino,
dialkylaminocarbonyl,
cycloalkyl,
cycloalkoxy,
cycloalkylthio,
cycloalkylamino,
alkenyl,
alkenyloxy,
alkynyl,
alkynyloxy,
phenylsulfonyl,
phenylsulfonyloxy or
phenylsulfonylamino;
5- or 6-membered heteroaryl, containing in addition to carbon ring members one to three nitrogen atoms or one or two nitrogen atoms and an oxygen or sulfur atom or an oxygen or sulfur atom as further ring members, eg. furyl, thienyl, pyrrolyl, pyrazolyl, imidazolyl, triazolyl, isoxazolyl, oxazolyl, oxadiazolyl, isothiazolyl, thiazolyl, thiadiazolyl, pyridyl, pyridazinyl, pyrimidyl, pyrazinyl or triazinyl, it being possible for these rings to carry one to four halogen atoms and/or one to three of the following radicals:
amino (—$NH_2$),
carboxyl (—$CO_2H$),
carbonylamino (—$CONH_2$),
cyano (—CN),
formyl (—CHO),
formylamino (—NHCHO),
hydroxyl (—OH),
isocyano (—NC),
nitro (—$NO_2$),
sulfoxyl (—$SO_3H$),
thiocarboxamido (—NHCOSH),
thiocyanato (—NCS),
alkyl,
haloalkyl,
alkylcarbonyl,
alkylcarbonyloxy,
alkylcarbonylthio,
alkylcarbonylamino,
alkylsulfonyl,
alkylsulfonyloxy,
alkylsulfonylamino,
alkoxy,
haloalkoxy,
alkoxycarbonyl,
alkoxyiminoalkyl,
alkylthio,
alkylthiocarbonyl,
alkylamino,
alkylaminocarbonyl,
dialkylamino,
dialkylaminocarbonyl,
cycloalkyl,
cycloalkoxy,
cycloalkylthio,
cycloalkylamino,
alkenyl,
alkenyloxy,
alkynyl,
alkynyloxy,
phenylsulfonyl,
phenylsulfonyloxy or
phenylsulfonylamino;

3. or for the case where the value of n is 0, $R^2$ is, additionally to the above meanings: halogen, $C_1$–$C_6$-alkoxy, $C_1$–$C_4$-alkylsulfoxyl or phenylsulfoxyl, the phenyl ring in turn being able to carry one to five halogen atoms and/or one to three of the following substituents: halogen, $C_1$–$C_4$-alkyl, $C_1$–$C_4$-haloalkyl, $C_1$–$C_4$-alkoxy, $C_1$–$C_4$-haloalkoxy, $C_3$–$C_6$-cycloalkyl, phenyl or benzyl.

In the above definitions of the substituents, collective terms were used which are generally representative of the following groups:

halogen: fluorine, chlorine, bromine and iodine;

alkyl: straight-chain or branched alkyl groups having 1 to 8, preferably 1 to 6, in particular 1 to 4 carbon atoms, eg. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 4 carbon atoms, it being possible for the hydrogen atoms in these groups to be partly or completely replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkylcarbonyl: straight-chain or branched alkyl groups having 1 to 8 carbon atoms as mentioned above in general and in particular, which are bonded to the structure via a carbonyl group (—CO—);

alkylcarbonyloxy: straight-chain or branched alkyl groups having 1 to 8 carbon atoms as mentioned above in general and in particular, which are bonded to the structure via a carbonyl group (—CO—O—); alkylcarbonylthio: straight-chain or branched alkyl groups having 1 to 8 carbon atoms as mentioned above in general and in particular, which are bonded to the structure via a carbonylthio group (—CO—S—);

alkylcarbonylamino: straight-chain or branched alkyl groups having 1 to 8 carbon atoms as mentioned above in general and in particular, which are bonded to the structure via a carbonylamino group (—CO—NH—);

alkylsulfonyl: straight-chain or branched alkyl groups having 1 to 8 carbon atoms as mentioned above in general and in particular, which are bonded to the structure via a sulfonyl group (—$SO_2$—);

alkylsulfonyloxy: straight-chain or branched alkyl groups having 1 to 8 carbon atoms as mentioned above in general and in particular, which are bonded to the structure via a sulfonyloxy group (—$SO_2$—);

alkylsulfonylamino: straight-chain or branched alkyl groups having 1 to 8 carbon atoms as mentioned above in general and in particular, which are bonded to the structure via a sulfonylamino group (—$SO_2NH$—);

alkoxy: straight-chain or branched alkoxy groups having 1 to 8, preferably 1 to 6, in particular 1 to 4 carbon atoms, eg. methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentoxy, 2-methyl-pentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

haloalkoxy: straight-chain or branched alkoxy groups having 1 to 4 carbon atoms, it being possible for the hydrogen atoms in these groups to be partly or completely replaced by halogen atoms as mentioned above, eg. $C_1$–$C_2$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy;

alkoxycarbonyl: straight-chain or branched alkoxy groups having 1 to 8 carbon atoms as mentioned above in general and in particular, which are bonded to the structure via a carbonyl group (—CO—);

alkoxyiminoalkyl: straight-chain or branched alkyl groups having 1 to 6 carbon atoms as mentioned above, which in the 1-position carry an alkyl group, preferably a $C_1$–$C_6$-alkyl group, in particular a $C_1$–$C_4$-alkyl group, or an alkoxyimino group (alkoxy-N═), preferably $C_1$–$C_6$-alkoxy-N═;

alkylthio: straight-chain or branched alkylthio groups having 1 to 8, preferably 1 to 6, in particular 1 to 4 carbon atoms, eg. methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

alkylthiocarbonyl: straight-chain or branched alkyl groups having 1 to 8 carbon atoms as mentioned above in general and in particular, which are bonded to the structure via a thiocarbonyl group (—S—CO—);

alkylamino: an amino group which carries a straight-chain or branched alkyl group having 1 to 8 carbon atoms as mentioned above in general and in particular;

alkylaminocarbonyl: straight-chain or branched alkyl groups having 1 to 8 carbon atoms as mentioned above in general and in particular, which are bonded to the structure via an aminocarbonyl group (—NH—CO—);

dialkylamino: an amino group which carries two straight-chain or branched alkyl groups which are independent of one another and in each case have 1 to 8, preferably 1 to 6, in particular 1 to 4 carbon atoms, eg. di-$C_1$–$C_4$-alkylamino such as N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl) amino, N-(1-methylpropyl)-N-(2-methylpropyl) amino, N-(1,1-dimethylethyl)-N-(1-methylpropyl) amino and N-(1,1-dimethylethyl)-N-(2-methylpropyl)amino;

dialkylaminocarbonyl: an amino group which carries two straight-chain or branched alkyl groups which are independent of one another as mentioned above in general and in particular in each case having 1 to 8 carbon atoms and is bonded to the structure via a carbonyl group (—CO—);

cycloalkyl: monocyclic alkyl groups having 3 to 8, preferably 3 to 6 carbon ring members, such as cyclopropyl, cyclobutyl, cyclopentyl, cyclohexyl, cycloheptyl and cyclooctyl;

cycloalkoxy: monocyclic alkyl groups having 3 to 8, preferably 3 to 6 carbon ring members, which are bonded to the structure via an oxy group (—O—);

cycloalkylamino: monocyclic alkyl groups having 3 to 8 carbon ring members which are bonded to the structure via an amino group (—NH—);

alkenyl: straight-chain or branched alkenyl groups having 2 to 10, preferably 2 to 8, in particular 2 to 6 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl und 1-ethyl-2-methyl-2-propenyl;

alkenyloxy: straight-chain or branched alkenyloxy groups having 2 to 8 carbon atoms and a double bond in any desired position, eg. $C_2$–$C_6$-alkenyloxy such as ethenyloxy, 1-propenyloxy, 2-propenyloxy, 1-methylethenyloxy, 1-butenyloxy, 2-butenyloxy, 3-butenyloxy, 1-methyl-1-propenyloxy, 2-methyl-1-propenyloxy, 1-methyl-2-propenyloxy, 2-methyl-2-propenyloxy, 1-pentenyloxy, 2-pentenyloxy, 3-pentenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy, 5-hexenyloxy, 1-methyl-1-pentenyloxy, 2-methyl-1-pentenyloxy, 3-methyl-1-pentenyloxy, 4-methyl-1-pentenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-1-butenyloxy, 1,2-dimethyl-2-butenyloxy, 1,2-dimethyl-3-butenyloxy, 1,3-dimethyl-1-butenyloxy, 1,3-dimethyl-2-butenyloxy, 1,3-dimethyl-3-butenyloxy, 2,2-dimethyl-3-butenyloxy, 2,3-dimethyl-1-butenyloxy, 2,3-dimethyl-2-butenyloxy, 2,3-dimethyl-3-butenyloxy, 3,3-dimethyl-1-butenyloxy, 3,3-dimethyl-2-butenyloxy, 1-ethyl-1-butenyloxy, 1-ethyl-2-butenyloxy, 1-ethyl-3-butenyloxy, 2-ethyl-1-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-1-propenyloxy and 1-ethyl-2-methyl-2-propenyloxy;

alkynyl: straight-chain or branched alkynyl groups having 2 to 10, preferably 2 to 8, in particular 2 to 6 carbon atoms and a triple bond in any desired position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

alkynyloxy: straight-chain or branched alkynyloxy groups having 2 to 10, preferably 2 to 8, in particular 2 to 6 carbon atoms and a double bond in any desired position, eg. $C_2$–$C_6$-alkynyloxy such as ethynyloxy, 1-propynyloxy, 2-propynyloxy, 1-butynyloxy, 2-butynyloxy, 3-butynyloxy, 1-methyl-2-propynyloxy, 1-pentynyloxy, 2-pentynyloxy, 3-pentynyloxy, 4-pentynyloxy, 1-methyl-2-butynyloxy, 1-methyl-3-butynyloxy, 2-methyl-3-butynyloxy, 3-methyl-1-butynyloxy, 1,1-dimethyl-2-propynyloxy, 1-ethyl-2-propynyloxy, 1-hexynyloxy, 2-hexynyloxy, 3-hexynyloxy, 4-hexynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-1-pentynyloxy, 3-methyl-4-pentynyloxy, 4-methyl-1-pentynyloxy, 4-methyl-2-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 3,3-dimethyl-1-butynyloxy, 1-ethyl-2-butynyloxy, 1-ethyl-3-butynyloxy, 2-ethyl-3-butynyloxy and 1-ethyl-1-methyl-2-propynyloxy;

phenylsulfonyl, phenylsulfonyloxy and phenylsulfonylamino: phenyl radicals which are bonded to the structure via a sulfonyl group (—$SO_2$—), a sulfonyloxy group (—$SO_3$—) or a sulfonylamino group (—$SO_2$—NH—).

Particularly preferred compounds I are those in which A is one of the radicals A.1, A.2, A.3, A.4, A.5, A.8, A.9, A.10, A.11, A.12 or A.15.

Compounds I are additionally preferred where A is unsubstituted or carries one or two of the following radicals R3: cyano, nitro, thiocarboxamides, halogen, preferably fluorine or chlorine, in particular chlorine; $C_1$–$C_4$-alkyl, preferably $C_1$–$C_3$-alkyl, in particular methyl; $C_1$–$C_2$-haloalkyl, in particular trifluoromethyl. In addition, compounds I are preferred where Z is $CHOCH_3$, $NOCH_3$ or $CHCH_3$.

In addition, compounds I are preferred where Y is oxygen.

Compounds I are additionally preferred where Z is $NOCH_3$ and Y is nitrogen, the nitrogen atom carrying one of the following radicals:

hydrogen;

$C_1$–$C_4$-alkyl, preferably $C_1$–$C_2$-alkyl, in particular methyl or $C_1$–$C_4$-alkoxy, preferably $C_1$–$C_2$-alkoxy, in particular methoxy.

Examples of naphthyl ethers of the formula I which are particularly preferred with respect to the use according to the invention are compiled in the following Tables 1 to 41:

Table 1

Compounds of the general formula I.1, where the combination of the substituents Z and $R^2$ and of the index n corresponds to one line of Table A

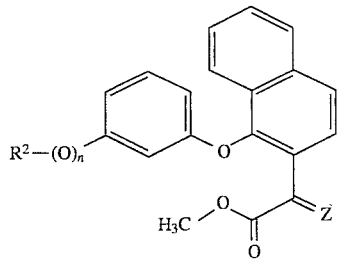

I.1

Table 2

Compounds of the general formula I.2, where the combination of the substituents $R^2$ and Z and of the index n corresponds to one line of Table A

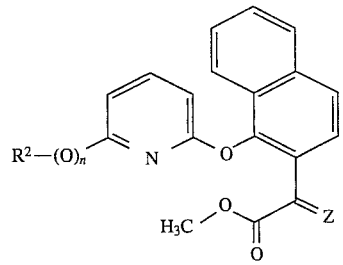

I.2

Table 3

Compounds of the general formula I.3, where the combination of the substituents $R^2$ and Z and of the index n corresponds to one line of Table A

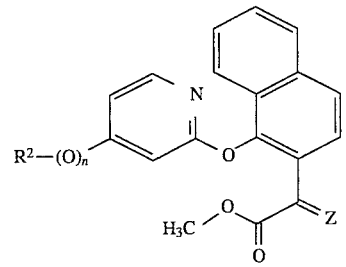

I.3

Table 4

Compounds of the general formula I.4, where the combination of the substituents $R^2$ and Z and of the index n corresponds to one line of Table A

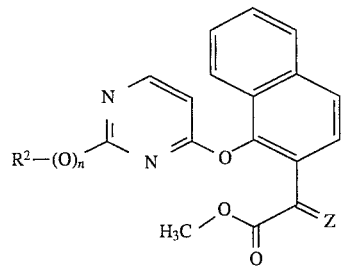

I.4

Table 5

Compounds of the general formula I.5, where the combination of the substituents $R^2$ and Z and of the index n corresponds to one line of Table A

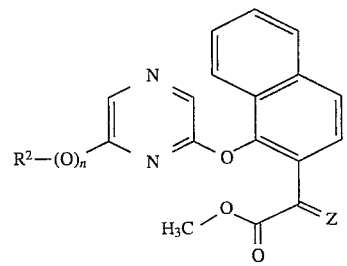

I.5

Table 6

Compounds of the general formula I.1, where the combination of the substituents $R^2$ and Z and of the index n corresponds to one line of Table A

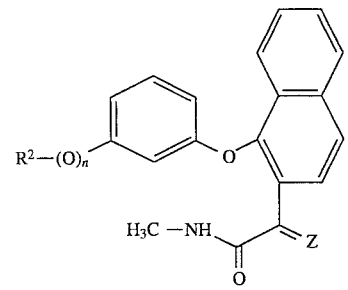

I.6

Table 7

Compounds of the general formula I.2, where the combination of the substituents $R^2$ and Z and of the index n corresponds to one line of Table A

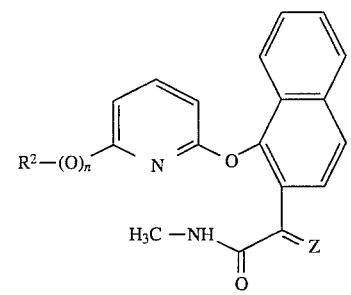

I.7

Table 8

Compounds of the general formula I.3, where the combination of the substituents $R^2$ and Z and of the index n corresponds to one line of Table A

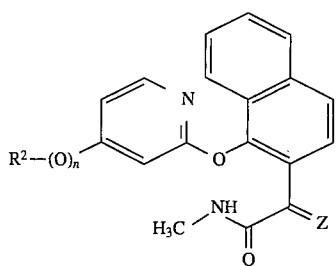

I.8

Table 9

Compounds of the general formula I.4, where the combination of the substituents $R^2$ and Z and of the index n corresponds to one line of Table A

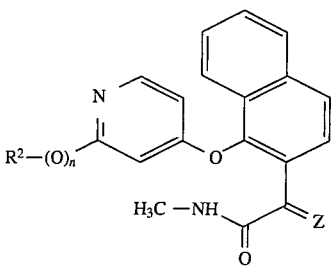

I.9

Table 10

Compounds of the general formula I.5, where the combination of the substituents $R^2$ and Z and of the index n corresponds to one line of Table A

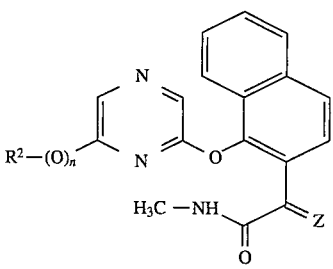

I.10

Table 11

Compounds of the general formula I.11, where the combination of the substituents $R^2$ and Z and of the index n corresponds to one line of Table A

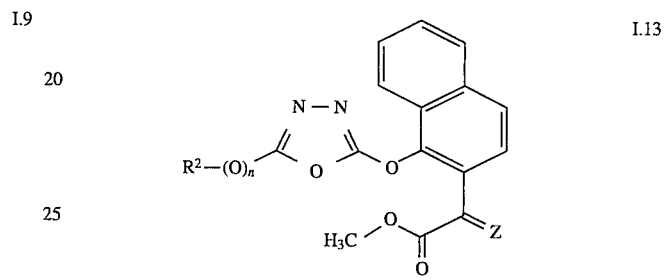

I.11

Table 12

Compounds of the general formula I.12, where the combination of the substituents $R^2$ and Z and of the index n corresponds to one line of Table A

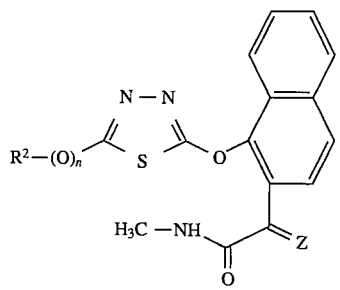

I.12

Table 13

Compounds of the general formula I.13, where the combination of the substituents $R^2$ and Z and of the index n corresponds to one line of Table A

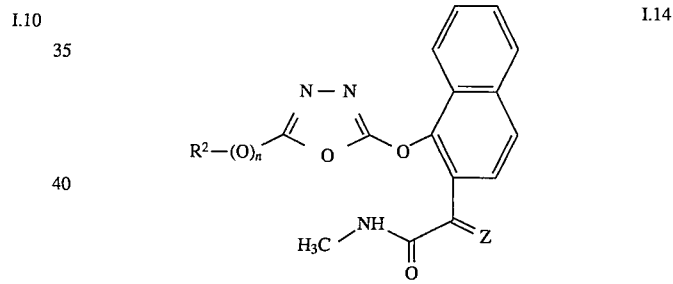

I.13

Table 14

Compounds of the general formula I.14, where the combination of the substituents $R^2$ and Z and of the index n corresponds to one line of Table A

I.14

Table 15

Compounds of the general formula .15, where the combination of the substituents $R^2$ and Z and of the index n corresponds to one line of Table A

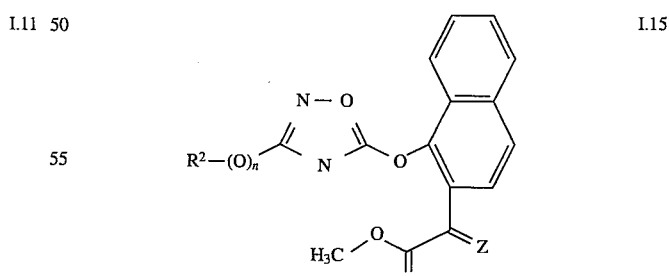

I.15

Table 16

Compounds of the general formula I.16, where the combination of the substituents $R^2$ and Z and of the index n corresponds to one line of Table A

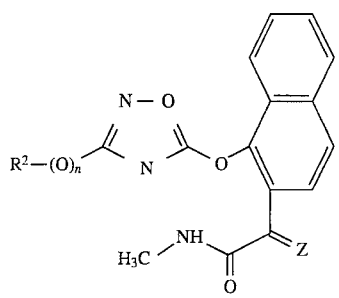

I.16

Table 17

Compounds of the general formula I.17, where the combination of the substituents $R^2$ and Z and of the index n corresponds to one line of Table A

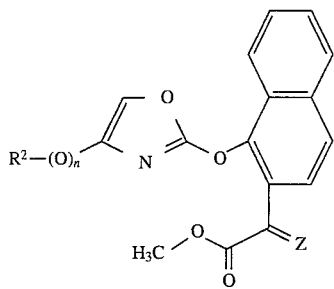

I.17

Table 18

Compounds of the general formula I.18, where the combination of the substituents $R^2$ and Z and of the index n corresponds to one line of Table A

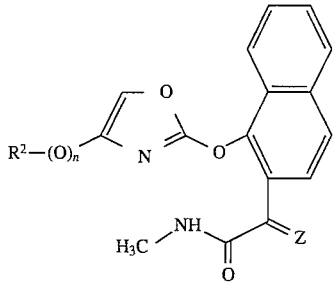

I.18

Table 19

Compounds of the general formula I.19, where the combination of the substituents $R^2$ and Z and of the index n corresponds to one line of Table A

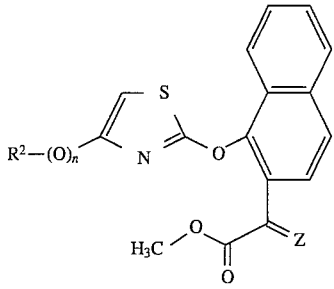

I.19

Table 20

Compounds of the general formula I.20, where the combination of the substituents $R^2$ and Z and of the index n corresponds to one line of Table B

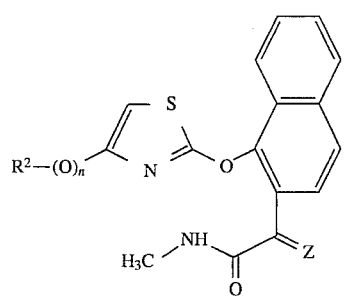

I.20

Table 21

Compounds of the general formula I.21, where the combination of the substituents $R^2$ and Z and of the index n corresponds to one line of Table B

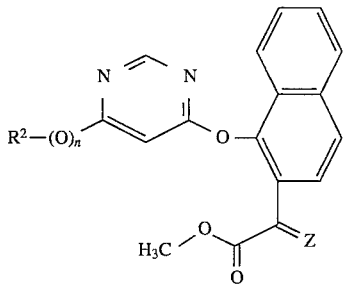

I.21

Table 22

Compounds of the general formula I.22, where the combination of the substituents $R^2$ and Z and of the index n corresponds to one line of Table B

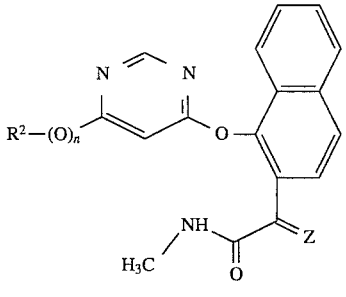

Table 23

Compounds of the general formula I.23, where the combination of the substituents $R^2$ and Z and of the index n corresponds to one line of Table B

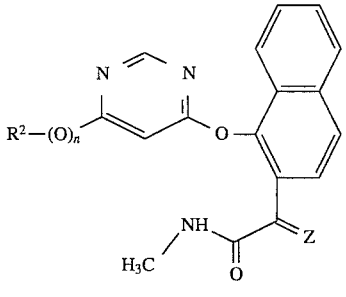

I.23

Table 24

Compounds of the general formula I.24, where the combination of the substituents $R^2$ and Z and of the index n corresponds to one line of Table B

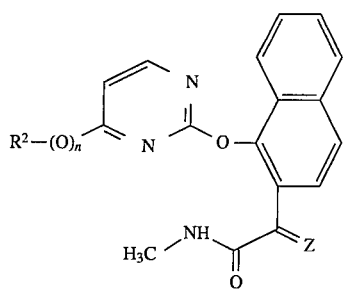

I.24

Table 25

Compounds of the general formula I.25, where the combination of the substituents U and Z and of the index n corresponds to one line of Table B

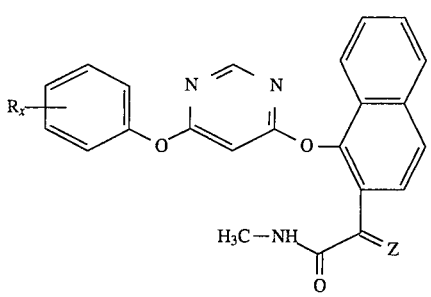

I.28

Table 29

Compounds of the general formula I.29, where the combination of the substituents $R_x$ and Z corresponds to one line of Table C

I.25

Table 26

Compounds of the general formula I.26, where the combination of the substituents $R^2$ and Z and of the index n corresponds to one line of Table B

I.29

Table 30

Compounds of the general formula I.30, where the combination of the substituents $R_x$ and Z corresponds to one line of Table C

I.26

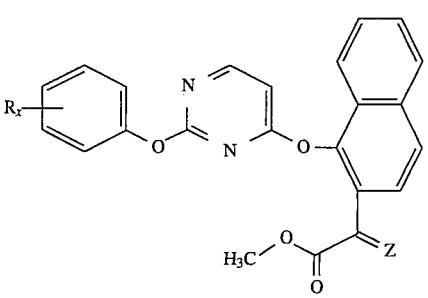

I.30

Table 27

Compounds of the general formula I.27, where the combination of the substituents $R^2$ and Z corresponds to one line of Table C

Table 31

Compounds of the general formula I.31, where the combination of the substituents $R_x$ and Z corresponds to one line of Table C

I.27

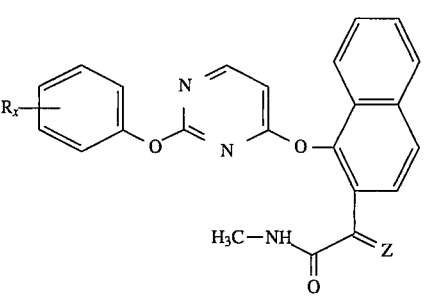

I.31

Table 28

Compounds of the general formula I.28, where the combination of the substituents $R_x$ and Z corresponds to one line of Table C

Table 32

Compounds of the general formula I.32, where the combination of the substituents $R_x$ and Z corresponds to one line of Table C

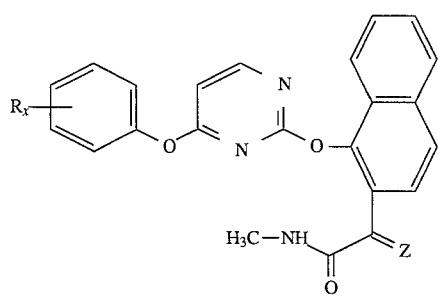

I.32

Table 33

Compounds of the general formula I.33, where the combination of the substituents $R_x$ and Z corresponds to one line of Table C

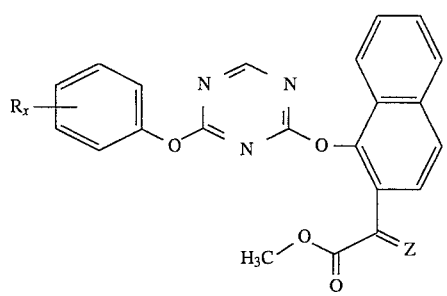

I.33

Table 34

Compounds of the general formula I.34, where the combination of the substituents $R_x$ and Z corresponds to one line of Table C

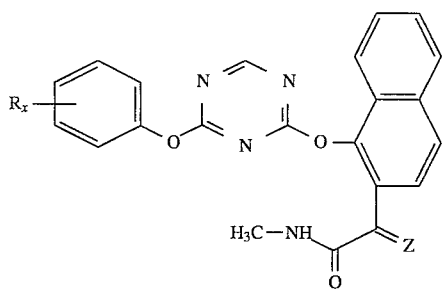

I.34

Table 35

Compounds of the general formula I.35, where the combination of the substituents $R_x$ and Z corresponds to one line of Table D

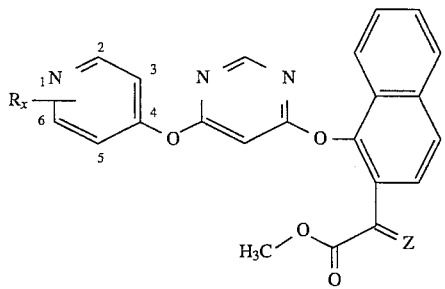

I.35

Table 36

Compounds of the general formula I.36, where the combination of the substituents $R_x$ and Z corresponds to one line of Table E

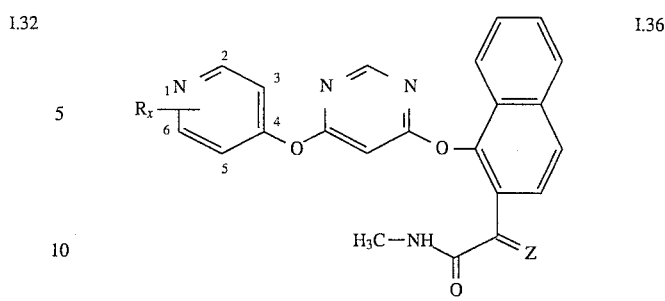

I.36

Table 37

Compounds of the general formula I.37, where the combination of the substituents $R_x$ and Z corresponds to one line of Table C

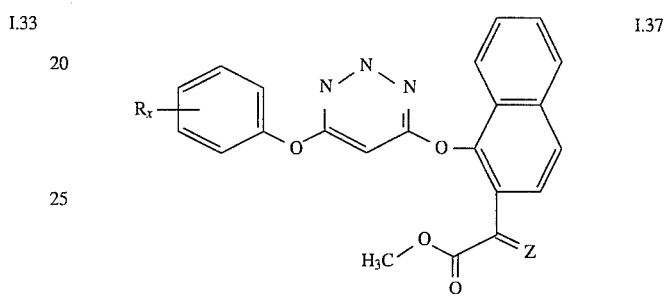

I.37

Table 38

Compounds of the general formula I.38, where the combination of the substituents $R_x$ and Z corresponds to one line of Table C

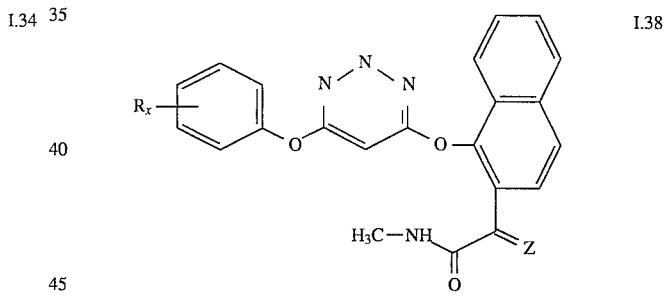

I.38

Table 39

Compounds of the general formula I.39, where the combination of the substituents R and Z and of the index n corresponds to one line of Table A

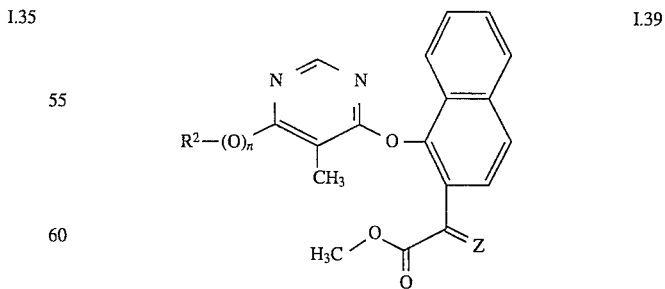

I.39

Table 40

Compounds of the general formula I.40, where the combination of the substituents $R_2$ and Z and of the index n corresponds to one line of Table A

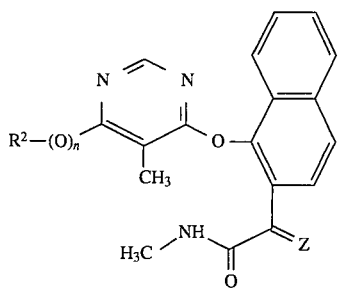

I.40

Table 41

Compounds of the general formula I.41, where the combination of the substituents R₂ and Z and of the index n corresponds to one line of Table A

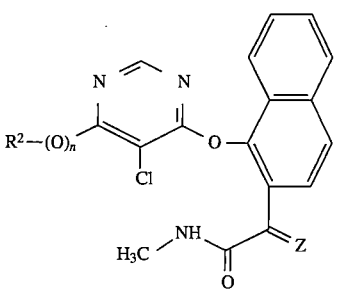

I.41

TABLE A

| No. | n | R² | Z |
|---|---|---|---|
| 1 | 0 | CN | NOCH₃ |
| 2 | 0 | CN | CHCH₃ |
| 3 | 0 | CN | CHOCH₃ |
| 4 | 0 | NO₂ | NOCH₃ |
| 5 | 0 | NO₂ | CHCH₃ |
| 6 | 0 | NO₂ | CHOCH₃ |
| 7 | 0 | CF₃ | NOCH₃ |
| 8 | 0 | CF₃ | CHCH₃ |
| 9 | 0 | CF₃ | CHOCH₃ |
| 10 | 0 | CHO | NOCH₃ |
| 11 | 0 | CHO | CHCH₃ |
| 12 | 0 | CHO | CHOCH₃ |
| 13 | 0 | COCH₃ | NOCH₃ |
| 14 | 0 | COCH₃ | CHCH₃ |
| 15 | 0 | COCH₃ | CHOCH₃ |
| 16 | 0 | CH=NOCH₃ | NOCH₃ |
| 17 | 0 | CH=NOCH₃ | CHCH₃ |
| 18 | 0 | CH=NOCH₃ | CHOCH₃ |
| 19 | 0 | C(CH₃)=NOCH₃ | NOCH₃ |
| 20 | 0 | C(CH₃)=NOCH₃ | CHCH₃ |
| 21 | 0 | C(CH₃)=NOCH₃ | CHOCH₃ |
| 22 | 0 | COOH | NOCH₃ |
| 23 | 0 | COOH | CHCH₃ |
| 24 | 0 | COOH | CHOCH₃ |
| 25 | 0 | COOCH₃ | NOCH₃ |
| 26 | 0 | COOCH₃ | CHCH₃ |
| 27 | 0 | COOCH₃ | CHOCH₃ |
| 28 | 0 | 3-F—C₆H₄ | NOCH₃ |
| 29 | 0 | 3-F—C₆H₄ | CHCH₃ |
| 30 | 0 | 3-F—C₆H₄ | CHOCH₃ |
| 31 | 0 | 3-Cl—C₆H₄ | NOCH₃ |
| 32 | 0 | 3-Cl—C₆H₄ | CHCH₃ |
| 33 | 0 | 3-Cl—C₆H₄ | CHOCH₃ |
| 34 | 0 | 3-CN—C₆H₄ | NOCH₃ |
| 35 | 0 | 3-CN—C₆H₄ | CHCH₃ |
| 36 | 0 | 3-CN—C₆H₄ | CHOCH₃ |
| 37 | 0 | 3-CSNH₂—C₆H₄ | NOCH₃ |
| 38 | 0 | 3-CSNH₂—C₆H₄ | CHCH₃ |
| 39 | 0 | 3-CSNH₂—C₆H₄ | CHOCH₃ |
| 40 | 0 | 3-CH₃—C₆H₄ | NOCH₃ |
| 41 | 0 | 3-CH₃—C₆H₄ | CHCH₃ |
| 42 | 0 | 3-CH₃—C₆H₄ | CHOCH₃ |
| 43 | 0 | 3-CH₃O—C₆H₄ | NOCH₃ |
| 44 | 0 | 3-CH₃O—C₆H₄ | CHCH₃ |
| 45 | 0 | 3-CH₃O—C₆H₄ | CHOCH₃ |
| 46 | 0 | C₆H₅SO₂ | NOCH₃ |
| 47 | 0 | C₆H₅SO₂ | CHCH₃ |
| 48 | 0 | C₆H₅SO₂ | CHOCH₃ |
| 49 | 1 | 2-F—C₆H₄ | NOCH₃ |
| 50 | 1 | 2-F—C₆H₄ | CHCH₃ |
| 51 | 1 | 2-F—C₆H₄ | CHOCH₃ |
| 52 | 1 | 2-Cl—C₆H₄ | NOCH₃ |
| 53 | 1 | 2-Cl—C₆H₄ | CHCH₃ |
| 54 | 1 | 2-Cl—C₆H₄ | CHOCH₃ |
| 55 | 1 | 2-Br—C₆H₄ | NOCH₃ |
| 56 | 1 | 2-Br—C₆H₄ | CHCH₃ |
| 57 | 1 | 2-Br—C₆H₄ | CHOCH₃ |
| 58 | 1 | 2-CN—C₆H₄ | NOCH₃ |
| 59 | 1 | 2-CN—C₆H₄ | CHCH₃ |
| 60 | 1 | 2-CN—C₆H₄ | CHOCH₃ |
| 61 | 1 | 2-NO₂—C₆H₄ | NOCH₃ |
| 62 | 1 | 2-NO₂—C₆H₄ | CHCH₃ |
| 63 | 1 | 2-NO₂—C₆H₄ | CHOCH₃ |
| 64 | 1 | 2-CF₃—C₆H₄ | NOCH₃ |
| 65 | 1 | 2-CF₃—C₆H₄ | CHCH₃ |
| 66 | 1 | 2-CF₃—C₆H₄ | CHOCH₃ |
| 67 | 1 | 2-CH₃—C₆H₄ | NOCH₃ |
| 68 | 1 | 2-CH₃—C₆H₄ | CHCH₃ |
| 69 | 1 | 2-CH₃C₆H₄ | CHOCH₃ |
| 70 | 1 | 2-C₂H₅—C₆H₄ | NOCH₃ |
| 71 | 1 | 2-C₂H₅—C₆H₄ | CHCH₃ |
| 72 | 1 | 2-C₂H₅—C₆H₄ | CHOCH₃ |
| 73 | 1 | 2-n-C₃H₇—C₆H₄ | NOCH₃ |
| 74 | 1 | 2-n-C₃H₇—C₆H₄ | CHCH₃ |
| 75 | 1 | 2-n-C₃H₇—C₆H₄ | CHOCH₃ |
| 76 | 1 | 2-CH₃O—C₆H₄ | NOCH₃ |
| 77 | 1 | 2-CH₃O—C₆H₄ | CHCH₃ |
| 78 | 1 | 2-CH₃O—C₆H₄ | CHOCH₃ |
| 79 | 1 | 2-CH₃S—C₆H₄ | NOCH₃ |
| 80 | 1 | 2-CH₃S—C₆H₄ | CHCH₃ |
| 81 | 1 | 2-CH₃S—C₆H₄ | CHOCH₃ |
| 82 | 1 | 2-CH₃SO₂—C₆H₄ | NOCH₃ |
| 83 | 1 | 2-CH₃SO₂—C₆H₄ | CHCH₃ |
| 84 | 1 | 2-CH₃SO₂—C₆H₄ | CHOCH₃ |
| 85 | 1 | 2-CHO—C₆H₄ | NOCH₃ |
| 86 | 1 | 2-CHO—C₆H₄ | CHCH₃ |
| 87 | 1 | 2-CHO—C₆H₄ | CHOCH₃ |
| 88 | 1 | 2-COCH₃—C₆H₄ | NOCH₃ |
| 89 | 1 | 2-COCH₃—C₆H₄ | CHCH₃ |
| 90 | 1 | 2-COCH₃—C₆H₄ | CHOCH₃ |
| 91 | 1 | 2-CH=NOCH₃—C₆H₄ | NOCH₃ |
| 92 | 1 | 2-CH=NOCH₃—C₆H₄ | CHCH₃ |
| 93 | 1 | 2-CH=NOCH₃—C₆H₄ | CHOCH₃ |
| 94 | 1 | 2-C(CH₃)=NOCH₃—C₆H₄ | NOCH₃ |
| 95 | 1 | 2-C(CH₃)=NOCH₃—C₆H₄ | CHCH₃ |
| 96 | 1 | 2-C(CH₃)=NOCH₃—C₆H₄ | CHOCH₃ |
| 97 | 1 | 2-COOH—C₆H₄ | NOCH₃ |
| 98 | 1 | 2-COOH—C₆H₄ | CHCH₃ |
| 99 | 1 | 2-COOH—C₆H₄ | CHOCH₃ |
| 100 | 1 | 2-COOCH₃—C₆H₄ | NOCH₃ |
| 101 | 1 | 2-COOCH₃—C₆H₄ | CHCH₃ |
| 102 | 1 | 2-COOCH₃—C₆H₄ | CHOCH₃ |
| 103 | 1 | 2-CONH₂—C₆H₄ | NOCH₃ |
| 104 | 1 | 2-CONH₂—C₆H₄ | CHCH₃ |
| 105 | 1 | 2-CONH₂—C₆H₄ | CHOCH₃ |
| 106 | 1 | 2-CSNH₂—C₆H₄ | NOCH₃ |
| 107 | 1 | 2-CSNH₂—C₆H₄ | CHCH₃ |
| 108 | 1 | 2-CSNH₂—C₆H₄ | CHOCH₃ |
| 109 | 1 | 2-CH₃COO—C₆H₄ | NOCH₃ |
| 110 | 1 | 2-CH₃COO—C₆H₄ | CHCH₃ |
| 111 | 1 | 2-CH₃COO—C₆H₄ | CHOCH₃ |
| 112 | 1 | 2-CH₃CONH—C₆H₄ | NOCH₃ |
| 113 | 1 | 2-CH₃CONH—C₆H₄ | CHCH₃ |
| 114 | 1 | 2-CH₃CONH—C₆H₄ | CHOCH₃ |
| 115 | 1 | 2-CH₃SO₂O—C₆H₄ | NOCH₃ |
| 116 | 1 | 2-CH₃SO₂O—C₆H₄ | CHCH₃ |
| 117 | 1 | 2-CH₃SO₂O—C₆H₄ | CHOCH₃ |
| 118 | 1 | 2-CH₃SO₂NH—C₆H₄ | NOCH₃ |
| 119 | 1 | 2-CH₃SO₂NH—C₆H₄ | CHCH₃ |
| 120 | 1 | 2-CH₃SO₂NH—C₆H₄ | CHOCH₃ |

TABLE A-continued

| No. | n | R² | Z |
|---|---|---|---|
| 121 | 1 | 2,6-Difluorophenyl | NOCH₃ |
| 122 | 1 | 2,6-Difluorophenyl | CHCH₃ |
| 123 | 1 | 2,6-Difluorophenyl | CHOCH₃ |
| 124 | 1 | 3,6-Difluorophenyl | NOCH₃ |
| 125 | 1 | 3,6-Difluorophenyl | CHCH₃ |
| 126 | 1 | 3,6-Difluorophenyl | CHOCH₃ |
| 127 | 1 | 3-Cl-Pyridin-2-yl | NOCH₃ |
| 128 | 1 | 3-Cl-Pyridin-2-yl | CHCH₃ |
| 129 | 1 | 3-Cl-Pyridin-2-yl | CHOCH₃ |
| 130 | 1 | 3-CN-Pyridin-2-yl | NOCH₃ |
| 131 | 1 | 3-CN-Pyridin-2-yl | CHCH₃ |
| 132 | 1 | 3-CN-Pyridin-2-yl | CHOCH₃ |
| 133 | 1 | 3-CH₃-Pyridin-2-yl | NOCH₃ |
| 134 | 1 | 3-CH₃-Pyridin-2-yl | CHCH₃ |
| 135 | 1 | 3-CH₃-Pyridin-2-yl | CHOCH₃ |
| 136 | 1 | 3-CH₃O-Pyridin-2-yl | NOCH₃ |
| 137 | 1 | 3-CH₃O-Pyridin-2-yl | CHCH₃ |
| 138 | 1 | 3-CH₃O-Pyridin-2-yl | CHOCH₃ |
| 139 | 1 | 3-CSNH₂-Pyridin-2-yl | NOCH₃ |
| 140 | 1 | 3-CSNH₂-Pyridin-2-yl | CHCH₃ |
| 141 | 1 | 3-CSNH₂-Pyridin-2-yl | CHOCH₃ |
| 142 | 1 | 4-F-Pyridin-3-yl | NOCH₃ |
| 143 | 1 | 4-F-Pyridin-3-yl | CHCH₃ |
| 144 | 1 | 4-F-Pyridin-3-yl | CHOCH₃ |
| 145 | 1 | 4-CN-Pyridin-3-yl | NOCH₃ |
| 146 | 1 | 4-CN-Pyridin-3-yl | CHCH₃ |
| 147 | 1 | 4-CN-Pyridin-3-yl | CHOCH₃ |
| 148 | 1 | 4-CH₃-Pyridin-3-yl | NOCH₃ |
| 149 | 1 | 4-CH₃-Pyridin-3-yl | CHCH₃ |
| 150 | 1 | 4-CH₃-Pyridin-3-yl | CHOCH₃ |
| 151 | 1 | Pyrimidin-2-yl | NOCH₃ |
| 152 | 1 | Pyrimidin-2-yl | CHCH₃ |
| 153 | 1 | Pyrimidin-2-yl | CHOCH₃ |
| 154 | 1 | 2-CH₃-Pyrimidin-2-yl | NOCH₃ |
| 155 | 1 | 2-CH₃-Pyrimidin-2-yl | CHCH₃ |
| 156 | 1 | 2-CH₃-Pyrimidin-2-yl | CHOCH₃ |
| 157 | 1 | CHF₂—CF₂ | NOCH₃ |
| 158 | 1 | CHF₂—CF₂ | CHCH₃ |
| 159 | 1 | CHF₂—CF₂ | CHOCH₃ |
| 160 | 0 | Br | NOCH₃ |
| 161 | 0 | CH₃ | NOCH₃ |
| 162 | 0 | C₆H₅ | NOCH₃ |
| 163 | 0 | Pyridin-2-yl | NOCH₃ |
| 164 | 0 | Pyrimidin-2-yl | NOCH₃ |
| 165 | 0 | (CH₃)₃ | NOCH₃ |
| 166 | 1 | CH₃ | NOCH₃ |
| 167 | 1 | C₂H₅ | NOCH₃ |
| 168 | 1 | n-C₃H₇ | NOCH₃ |
| 169 | 1 | i-C₃H₇ | NOCH₃ |
| 170 | 1 | Pyridin-2-yl | NOCH₃ |
| 171 | 1 | 1-Pyridin-3-yl | NOCH₃ |
| 172 | 1 | 2-F-Pyridin-3-yl | NOCH₃ |
| 173 | 1 | 2-Cl-Pyridin-3-yl | NOCH₃ |
| 174 | 1 | 2-CN-Pyridin-3-yl | NOCH₃ |
| 175 | 1 | 2-CH₃-Pyridin-3-yl | NOCH₃ |
| 176 | 1 | 2-CH₃O-Pyridin-3-yl | NOCH₃ |
| 177 | 1 | 2-CSNH₂-Pyridin-3-yl | NOCH₃ |

TABLE B

| No. | n | R² | Z |
|---|---|---|---|
| 1 | 0 | F | NOCH₃ |
| 2 | 0 | F | CHCH₃ |
| 3 | 0 | F | CHOCH₃ |
| 4 | 0 | Cl | NOCH₃ |
| 5 | 0 | Cl | CHCH₃ |
| 6 | 0 | Cl | CHOCH₃ |
| 7 | 0 | Br | NOCH₃ |
| 8 | 0 | Br | CHCH₃ |
| 9 | 0 | Br | CHOCH₃ |
| 10 | 0 | CN | NOCH₃ |
| 11 | 0 | CN | CHCH₃ |
| 12 | 0 | CN | CHOCH₃ |
| 13 | 0 | NO₂ | NOCH₃ |
| 14 | 0 | NO₂ | CHCH₃ |
| 15 | 0 | NO₂ | CHOCH₃ |
| 16 | 0 | CF₃ | NOCH₃ |
| 17 | 0 | CF₃ | CHCH₃ |
| 18 | 0 | CF₃ | CHOCH₃ |
| 19 | 0 | CHO | NOCH₃ |
| 20 | 0 | CHO | CHCH₃ |
| 21 | 0 | CHO | CHOCH₃ |
| 22 | 0 | COCH₃ | NOCH₃ |
| 23 | 0 | COCH₃ | CHCH₃ |
| 24 | 0 | COCH₃ | CHOCH₃ |
| 25 | 0 | CH=NOCH₃ | NOCH₃ |
| 26 | 0 | CH=NOCH₃ | CHCH₃ |
| 27 | 0 | CH=NOCH₃ | CHOCH₃ |
| 28 | 0 | C(CH₃)=NOCH₃ | NOCH₃ |
| 29 | 0 | C(CH₃)=NOCH₃ | CHCH₃ |
| 30 | 0 | C(CH₃)=NOCH₃ | CHOCH₃ |
| 31 | 0 | COOH | NOCH₃ |
| 32 | 0 | COOH | CHCH₃ |
| 33 | 0 | COOH | CHOCH₃ |
| 34 | 0 | COOCH₃ | NOCH₃ |
| 35 | 0 | COOCH₃ | CHCH₃ |
| 36 | 0 | COOCH₃ | CHOCH₃ |
| 37 | 0 | C₆H₅ | NOCH₃ |
| 38 | 0 | C₆H₅ | CHCH₃ |
| 39 | 0 | C₆H₅ | CHOCH₃ |
| 40 | 0 | 3-F—C₆H₄ | NOCH₃ |
| 41 | 0 | 3-F—C₆H₄ | CHCH₃ |
| 42 | 0 | 3-F—C₆H₄ | CHOCH₃ |
| 43 | 0 | 3-Cl—C₆H₄ | NOCH₃ |
| 44 | 0 | 3-Cl—C₆H₄ | CHCH₃ |
| 45 | 0 | 3-Cl—C₆H₄ | CHOCH₃ |
| 46 | 0 | 3-CSNH₂—C₆H₄ | NOCH₃ |
| 47 | 0 | 3-CSNH₂—C₆H₄ | CHCH₃ |
| 48 | 0 | 3-CSNH₂—C₆H₄ | CHOCH₃ |
| 49 | 0 | 3-CH₃—C₆H₄ | NOCH₃ |
| 50 | 0 | 3-CH₃—C₆H₄ | CHCH₃ |
| 51 | 0 | 3-CH₃—C₆H₄ | CHOCH₃ |
| 52 | 0 | 3-CH₃O-C₆H₄ | NOCH₃ |
| 53 | 0 | 3-CH₃O-C₆H₄ | CHCH₃ |
| 54 | 0 | 3-CH₃O-C₆H₄ | CHOCH₃ |
| 55 | 0 | C₆H₅SO₂ | NOCH₃ |
| 56 | 0 | C₆H₅SO₂ | CHCH₃ |
| 57 | 0 | C₆H₅SO₂ | CHOCH₃ |
| 58 | 0 | C₆H₅—CH(OH) | NOCH₃ |
| 59 | 0 | C₆H₅—CH(OH) | CHCH₃ |
| 60 | 0 | C₆H₅—CH(OH) | CHOCH₃ |
| 61 | 0 | 2-C₂H₅—C₆H₄ | NOCH₃ |
| 62 | 0 | 2-C₂H₅—C₆H₄ | CHCH₃ |
| 63 | 0 | 2-C₂H₅—C₆H₄ | CHOCH₃ |
| 64 | 0 | CH₃ | NOCH₃ |
| 65 | 0 | CH₃ | CHCH₃ |
| 66 | 0 | CH₃ | CHOCH₃ |
| 67 | 0 | C₂H₅ | NOCH₃ |
| 68 | 0 | C₂H₅ | CHCH₃ |
| 69 | 0 | C₂H₅ | CHOCH₃ |
| 70 | 0 | n-C₃H₇ | NOCH₃ |
| 71 | 0 | n-C₃H₇ | CHCH₃ |
| 72 | 0 | n-C₃H₇ | CHOCH₃ |
| 73 | 0 | i-C₃H₇ | NOCH₃ |
| 74 | 0 | i-C₃H₇ | CHCH₃ |
| 75 | 0 | i-C₃H₇ | CHOCH₃ |
| 76 | 0 | CHF₂CF₂ | NOCH₃ |
| 77 | 0 | CHF₂CF₂ | CHCH₃ |
| 78 | 0 | CHF₂CF₂ | CHOCH₃ |
| 79 | 0 | Pyrimidin-2-yl | NOCH₃ |
| 80 | 0 | Pyrimidin-2-yl | CHCH₃ |
| 81 | 0 | Pyrimidin-2-yl | CHOCH₃ |
| 82 | 0 | 5-CH₃-Pyrimidin-2-yl | NOCH₃ |
| 83 | 0 | 5-CH₃-Pyrimidin-2-yl | CHCH₃ |
| 84 | 0 | 5-CH₃-Pyrimidin-2-yl | CHOCH₃ |
| 85 | 0 | C(CH₃)₃ | NOCH₃ |
| 86 | 0 | Pyrimidin-2-yl | CHCH₃ |
| 87 | 0 | Pyrimidin-2-yl | CHOCH₃ |
| 88 | 0 | OCH₃ | NOCH₃ |

TABLE B-continued

| No. | n | $R^2$ | Z |
|---|---|---|---|
| 89 | 0 | $OCH_3$ | $CHCH_3$ |
| 90 | 0 | $OCH_3$ | $CHOCH_3$ |

TABLE C

| No. | $R_x$ | Z |
|---|---|---|
| 1 | 2-F | $NOCH_3$ |
| 2 | 2-F | $CHCH_3$ |
| 3 | 2-F | $CHOCH_3$ |
| 4 | 3-F | $NOCH_3$ |
| 5 | 3-F | $CHCH_3$ |
| 6 | 3-F | $CHOCH_3$ |
| 7 | 2-Cl | $NOCH_3$ |
| 8 | 2-Cl | $CHCH_3$ |
| 9 | 2-Cl | $CHOCH_3$ |
| 10 | 3-Cl | $NOCH_3$ |
| 11 | 3-Cl | $CHCH_3$ |
| 12 | 3-Cl | $CHOCH_3$ |
| 13 | 2-Br | $NOCH_3$ |
| 14 | 2-Br | $CHCH_3$ |
| 15 | 2-Br | $CHOCH_3$ |
| 16 | 2-Cyano | $NOCH_3$ |
| 17 | 2-Cyano | $CHCH_3$ |
| 18 | 2-Cyano | $CHOCH_3$ |
| 19 | 3-Cyano | $NOCH_3$ |
| 20 | 3-Cyano | $CHCH_3$ |
| 21 | 3-Cyano | $CHOCH_3$ |
| 22 | 2-Isocyano | $NOCH_3$ |
| 23 | 2-Isocyano | $CHCH_3$ |
| 24 | 2-Isocyano | $CHOCH_3$ |
| 25 | $2-NO_2$ | $NOCH_3$ |
| 26 | $2-NO_2$ | $CHCH_3$ |
| 27 | $2-NO_2$ | $CHOCH_3$ |
| 28 | $3-NO_2$ | $NOCH_3$ |
| 29 | $3-NO_2$ | $CHCH_3$ |
| 30 | $3-NO_2$ | $CHOCH_3$ |
| 31 | $2-NH_2$ | $NOCH_3$ |
| 32 | $2-NH_2$ | $CHCH_3$ |
| 33 | $2-NH_2$ | $CHOCH_3$ |
| 34 | $3-NH(CH_3)$ | $NOCH_3$ |
| 35 | $3-NH(CH_3)$ | $CHCH_3$ |
| 36 | $3-NH(CH_3)$ | $CHOCH_3$ |
| 37 | $2-N(CH_3)_2$ | $NOCH_3$ |
| 38 | $2-N(CH_3)_2$ | $CHCH_3$ |
| 39 | $2-N(CH_3)_2$ | $CHOCH_3$ |
| 40 | 2-NHCHO | $NOCH_3$ |
| 41 | 2-NHCHO | $CHCH_3$ |
| 42 | 2-NHCHO | $CHOCH_3$ |
| 43 | $2-NH-COCH_3$ | $NOCH_3$ |
| 44 | $2-NH-COCH_3$ | $CHCH_3$ |
| 45 | $2-NH-COCH_3$ | $CHOCH_3$ |
| 46 | $3-NH-COC_6H_5$ | $NOCH_3$ |
| 47 | $3-NH-COC_6H_5$ | $CHCH_3$ |
| 48 | $3-NH-COC_6H_5$ | $CHOCH_3$ |
| 49 | $2-NH-CONH_2$ | $NOCH_3$ |
| 50 | $2-NH-CONH_2$ | $CHCH_3$ |
| 51 | $2-NH-CONH_2$ | $CHOCH_3$ |
| 52 | $3-NH-CONH(C_2H_5)$ | $NOCH_3$ |
| 53 | $3-NH-CONH(C_2H_5)$ | $CHCH_3$ |
| 54 | $3-NH-CONH(C_2H_5)$ | $CHOCH_3$ |
| 55 | $2-NH-SO_2CH_3$ | $NOCH_3$ |
| 56 | $2-NH-SO_2CH_3$ | $CHCH_3$ |
| 57 | $2-NH-SO_2CH_3$ | $CHOCH_3$ |
| 58 | $3-NH-SO_2CH_3$ | $NOCH_3$ |
| 59 | $3-NH-SO_2CH_3$ | $CHCH_3$ |
| 60 | $3-NH-SO_2CH_3$ | $CHOCH_3$ |
| 61 | 2-OH | $NOCH_3$ |
| 62 | 2-OH | $CHCH_3$ |
| 63 | 2-OH | $CHOCH_3$ |
| 64 | 3-OH | $NOCH_3$ |
| 65 | 3-OH | $CHCH_3$ |
| 66 | 3-OH | $CHOCH_3$ |
| 67 | $2-OCH_3$ | $NOCH_3$ |
| 68 | $2-OCH_3$ | $CHCH_3$ |
| 69 | $2-OCH_3$ | $CHOCH_3$ |
| 70 | $3-OCH_3$ | $NOCH_3$ |
| 71 | $3-OCH_3$ | $CHCH_3$ |
| 72 | $3-OCH_3$ | $CHOCH_3$ |
| 73 | $2-OC_2H_5$ | $NOCH_3$ |
| 74 | $2-OC_2H_5$ | $CHCH_3$ |
| 75 | $2-OC_2H_5$ | $CHOCH_3$ |
| 76 | $2-(2-F-C_6H_4O)$ | $NOCH_3$ |
| 77 | $2-(2-F-C_6H_4O)$ | $CHCH_3$ |
| 78 | $2-(2-F-C_6H_4O)$ | $CHOCH_3$ |
| 79 | $2-OCOCH_3$ | $NOCH_3$ |
| 80 | $2-OCOCH_3$ | $CHCH_3$ |
| 81 | $2-OCOCH_3$ | $CHOCH_3$ |
| 82 | $2-OSO_2CH_3$ | $NOCH_3$ |
| 83 | $2-OSO_2CH_3$ | $CHCH_3$ |
| 84 | $2-OSO_2CH_3$ | $CHOCH_3$ |
| 85 | $3-(4-CH_3-C_6SO_2O)$ | $NOCH_3$ |
| 86 | $3-(4-CH_3-C_6SO_2O)$ | $CHCH_3$ |
| 87 | $3-(4-CH_3-C_6SO_2O)$ | $CHOCH_3$ |
| 88 | 2-SCN | $NOCH_3$ |
| 89 | 2-SCN | $CHCH_3$ |
| 90 | 2-SCN | $CHOCH_3$ |
| 91 | 3-SCN | $NOCH_3$ |
| 92 | 3-SCN | $CHCH_3$ |
| 93 | 3-SCN | $CHOCH_3$ |
| 94 | $2-SCH_3$ | $NOCH_3$ |
| 95 | $2-SCH_3$ | $CHCH_3$ |
| 96 | $2-SCH_3$ | $CHOCH_3$ |
| 97 | $3-SCH_3$ | $NOCH_3$ |
| 98 | $3-SCH_3$ | $CHCH_3$ |
| 99 | $3-SCH_3$ | $CHOCH_3$ |
| 100 | $2-S(O)CH_3$ | $NOCH_3$ |
| 101 | $2-S(O)CH_3$ | $CHCH_3$ |
| 102 | $2-S(O)CH_3$ | $CHOCH_3$ |
| 103 | $2-SO_2CH_3$ | $NOCH_3$ |
| 104 | $2-SO_2CH_3$ | $CHCH_3$ |
| 105 | $2-SO_2CH_3$ | $CHOCH_3$ |
| 106 | 2-CHO | $NOCH_3$ |
| 107 | 2-CHO | $CHCH_3$ |
| 108 | 2-CHO | $CHOCH_3$ |
| 109 | 3-CHO | $NOCH_3$ |
| 110 | 3-CHO | $CHCH_3$ |
| 111 | 3-CHO | $CHOCH_3$ |
| 112 | $2-COCH_3$ | $NOCH_3$ |
| 113 | $2-COCH_3$ | $CHCH_3$ |
| 114 | $2-COCH_3$ | $CHOCH_3$ |
| 115 | $3-COC_6H_5$ | $NOCH_3$ |
| 116 | $3-COC_6H_5$ | $CHCH_3$ |
| 117 | $3-COC_6H_5$ | $CHOCH_3$ |
| 118 | 2-(E)-CH=NOH | $NOCH_3$ |
| 119 | 2-(E)-CH=NOH | $CHCH_3$ |
| 120 | 2-(E)-CH=NOH | $CHOCH_3$ |
| 121 | 3-(E)-CH=NOH | $NOCH_3$ |
| 122 | 3-(E)-CH=NOH | $CHCH_3$ |
| 123 | 3-(E)-CH=NOH | $CHOCH_3$ |
| 124 | $2-(E)-CH=NOCH_3$ | $NOCH_3$ |
| 125 | $2-(E)-CH=NOCH_3$ | $CHCH_3$ |
| 126 | $2-(E)-CH=NOCH_3$ | $CHOCH_3$ |
| 127 | $2-(E)-C(CH_3)=NOH$ | $NOCH_3$ |
| 128 | $2-(E)-C(CH_3)=NOH$ | $CHCH_3$ |
| 129 | $2-(E)-C(CH_3)=NOH$ | $CHOCH_3$ |
| 130 | $2-CONH_2$ | $NOCH_3$ |
| 131 | $2-CONH_2$ | $CHCH_3$ |
| 132 | $2-CONH_2$ | $CHOCH_3$ |
| 133 | $3-CONH(CH_3)$ | $NOCH_3$ |
| 134 | $3-CONH(CH_3)$ | $CHCH_3$ |
| 135 | $3-CONH(CH_3)$ | $CHOCH_3$ |
| 136 | $2-CSNH_2$ | $NOCH_3$ |
| 137 | $2-CSNH_2$ | $CHCH_3$ |
| 138 | $2-CSNH_2$ | $CHOCH_3$ |
| 139 | $2-CSNH(CH_3)$ | $NOCH_3$ |
| 140 | $2-CSNH(CH_3)$ | $CHCH_3$ |
| 141 | $2-CSNH(CH_3)$ | $CHOCH_3$ |
| 142 | $2-CH_3$ | $NOCH_3$ |
| 143 | $2-CH_3$ | $CHCH_3$ |
| 144 | $2-CH_3$ | $CHOCH_3$ |
| 145 | $3-CH_3$ | $NOCH_3$ |

TABLE C-continued

| No. | $R_x$ | Z |
|---|---|---|
| 146 | 3-CH$_3$ | CHCH$_3$ |
| 147 | 3-CH$_3$ | CHOCH$_3$ |
| 148 | 3-C$_2$H$_5$ | NOCH$_3$ |
| 149 | 3-C$_2$H$_5$ | CHCH$_3$ |
| 150 | 3-C$_2$H$_5$ | CHOCH$_3$ |
| 151 | 3-CH$_2$F | NOCH$_3$ |
| 152 | 3-CH$_2$F | CHCH$_3$ |
| 153 | 3-CH$_2$F | CHOCH$_3$ |
| 154 | 2-CH$_2$Br | NOCH$_3$ |
| 155 | 2-CH$_2$Br | CHCH$_3$ |
| 156 | 2-CH$_2$Br | CHOCH$_3$ |
| 157 | 2-CH$_2$Cl | NOCH$_3$ |
| 158 | 2-CH$_2$Cl | CHCH$_3$ |
| 159 | 2-CH$_2$Cl | CHOCH$_3$ |
| 160 | 2-CH$_2$CN | NOCH$_3$ |
| 161 | 2-CH$_2$CN | CHCH$_3$ |
| 162 | 2-CH$_2$CN | CHOCH$_3$ |
| 163 | 2-CH$_2$OH | NOCH$_3$ |
| 164 | 2-CH$_2$OH | CHCH$_3$ |
| 165 | 2-CH$_2$OH | CHOCH$_3$ |
| 166 | 2-CH$_2$OCH$_3$ | NOCH$_3$ |
| 167 | 2-CH$_2$OCH$_3$ | CHCH$_3$ |
| 168 | 2-CH$_2$OCH$_3$ | CHOCH$_3$ |
| 169 | 2-CH$_2$OCOCH$_3$ | NOCH$_3$ |
| 170 | 2-CH$_2$OCOCH$_3$ | CHCH$_3$ |
| 171 | 2-CH$_2$OCOCH$_3$ | CHOCH$_3$ |
| 172 | 3-CH$_2$CN | NOCH$_3$ |
| 173 | 3-CH$_2$CN | CHCH$_3$ |
| 174 | 3-CH$_2$CN | CHOCH$_3$ |
| 175 | 2-CH$_2$OH | NOCH$_3$ |
| 176 | 2-CH$_2$OH | CHCH$_3$ |
| 177 | 2-CH$_2$OH | CHOCH$_3$ |
| 178 | 3-CH$_2$OCH$_3$ | NOCH$_3$ |
| 179 | 3-CH$_2$OCH$_3$ | CHCH$_3$ |
| 180 | 3-CH$_2$OCH$_3$ | CHOCH$_3$ |
| 181 | 2-CH=CH$_2$ | NOCH$_3$ |
| 182 | 2-CH=CH$_2$ | CHCH$_3$ |
| 183 | 2-CH=CH$_2$ | CHOCH$_3$ |
| 184 | 2-CH$_2$—CH=CH$_2$ | NOCH$_3$ |
| 185 | 2-CH$_2$—CH=CH$_2$ | CHCH$_3$ |
| 186 | 2-CH$_2$—CH=CH$_2$ | CHOCH$_3$ |
| 187 | 2-C≡CH | NOCH$_3$ |
| 188 | 2-C≡CH | CHCH$_3$ |
| 189 | 2-C≡CH | CHOCH$_3$ |
| 190 | 2-CH$_2$=CH | NOCH$_3$ |
| 191 | 2-CH$_2$=CH | CHCH$_3$ |
| 192 | 2-CH$_2$=CH | CHOCH$_3$ |
| 193 | 3-CH$_2$C(CH$_3$)=CH$_2$ | NOCH$_3$ |
| 194 | 3-CH$_2$C(CH$_3$)=CH$_2$ | CHCH$_3$ |
| 195 | 3-CH$_2$C(CH$_3$)=CH$_2$ | CHOCH$_3$ |
| 196 | 2-OCH$_2$CH=CH$_2$ | NOCH$_3$ |
| 197 | 2-OCH$_2$CH=CH$_2$ | CHCH$_3$ |
| 198 | 2-OCH$_2$CH=CH$_2$ | CHOCH$_3$ |
| 199 | 3-OCH$_2$CH=CH$_2$ | NOCH$_3$ |
| 200 | 3-OCH$_2$CH=CH$_2$ | CHCH$_3$ |
| 201 | 3-OCH$_2$CH=CH$_2$ | CHOCH$_3$ |
| 202 | 2-C$_6$H$_5$ | NOCH$_3$ |
| 203 | 2-C$_6$H$_5$ | CHCH$_3$ |
| 204 | 2-C$_6$H$_5$ | CHOCH$_3$ |
| 205 | 3-C$_6$H$_5$ | NOCH$_3$ |
| 206 | 3-C$_6$H$_5$ | CHCH$_3$ |
| 207 | 3-C$_6$H$_5$ | CHOCH$_3$ |
| 208 | 2-C$_6$H$_5$O | NOCH$_3$ |
| 209 | 2-C$_6$H$_5$O | CHCH$_3$ |
| 210 | 2-C$_6$H$_5$O | CHOCH$_3$ |
| 211 | 3-C$_6$H$_5$O | NOCH$_3$ |
| 212 | 3-C$_6$H$_5$O | CHCH$_3$ |
| 213 | 3-C$_6$H$_5$O | CHOCH$_3$ |
| 214 | 2-(4-Cl—C$_6$H$_4$O) | NOCH$_3$ |
| 215 | 2-(4-Cl—C$_6$H$_4$O) | CHCH$_3$ |
| 216 | 2-(4-Cl—C$_6$H$_4$O) | CHOCH$_3$ |
| 217 | 2-C$_6$H$_5$CH$_2$O | NOCH$_3$ |
| 218 | 2-C$_6$H$_5$CH$_2$O | CHCH$_3$ |
| 219 | 2-C$_6$H$_5$CH$_2$O | CHOCH$_3$ |
| 220 | 2-OCH$_3$, 3-OCH$_3$ | NOCH$_3$ |
| 221 | 2-OCH$_3$, 3-OCH$_3$ | CHCH$_3$ |
| 222 | 2-OCH$_3$, 3-OCH$_3$ | CHOCH$_3$ |
| 223 | 2-Cyano, 5-Cl | NOCH$_3$ |
| 224 | 2-Cyano, 5-Cl | CHCH$_3$ |
| 225 | 2-Cyano, 5-Cl | CHOCH$_3$ |
| 226 | 2-Cyano, 6-cyano | NOCH$_3$ |
| 227 | 2-Cyano, 6-cyano | CHCH$_3$ |
| 228 | 2-Cyano, 6-cyano | CHOCH$_3$ |
| 229 | 2-F, 5-Cl | NOCH$_3$ |
| 230 | 2-F, 5-Cl | CHCH$_3$ |
| 231 | 2-F, 5-Cl | CHOCH$_3$ |
| 232 | 3-OCH$_3$, 5-OCH$_3$ | NOCH$_3$ |
| 233 | 3-OCH$_3$, 5-OCH$_3$ | CHCH$_3$ |
| 234 | 3-OCH$_3$, 5-OCH$_3$ | CHOCH$_3$ |
| 235 | 2-NO$_2$, 3-OCH$_3$ | NOCH$_3$ |
| 236 | 2-NO$_2$, 3-OCH$_3$ | CHCH$_3$ |
| 237 | 2-NO$_2$, 3-OCH$_3$ | CHOCH$_3$ |
| 238 | 3-OCH$_2$, 5-cyano | NOCH$_3$ |
| 239 | 3-OCH$_2$, 5-cyano | CHCH$_3$ |
| 240 | 3-OCH$_2$, 5-cyano | CHOCH$_3$ |
| 241 | 2-CO$_2$CH$_3$ | NOCH$_3$ |
| 242 | 2-CO$_2$CH$_3$ | CHCH$_3$ |
| 243 | 2-CO$_2$CH$_3$ | CHOCH$_3$ |
| 244 | 2-I | NOCH$_3$ |
| 245 | 2-I | CHCH$_3$ |
| 246 | 2-I | CHOCH$_3$ |
| 247 | 2-CF$_3$ | NOCH$_3$ |
| 248 | 2-CF$_3$ | CHCH$_3$ |
| 249 | 2-CF$_3$ | CHOCH$_3$ |
| 250 | 2-i-C$_3$H$_7$ | NOCH$_3$ |
| 251 | 2-i-C$_3$H$_7$ | CHCH$_3$ |
| 252 | 2-i-C$_3$H$_7$ | CHOCH$_3$ |
| 253 | 2-i-C$_3$H$_7$O | NOCH$_3$ |
| 254 | 2-i-C$_3$H$_7$O | CHCH$_3$ |
| 255 | 2-i-C$_3$H$_7$O | CHOCH$_3$ |
| 256 | 2-F, 6-F | NOCH$_3$ |
| 257 | 2-F, 6-F | CHCH$_3$ |
| 258 | 2-F, 6-F | CHOCH$_3$ |
| 259 | 2-F, 3-F | NOCH$_3$ |
| 260 | 2-F, 3-F | CHCH$_3$ |
| 261 | 2-F, 3-F | CHOCH$_3$ |
| 262 | 2-n-C$_3$H$_7$O | NOCH$_3$ |
| 263 | 2-n-C$_3$H$_7$O | CHCH$_3$ |
| 264 | 2-n-C$_3$H$_7$O | CHOCH$_3$ |
| 265 | 2-n-C$_4$H$_9$O | NOCH$_3$ |
| 266 | 2-n-C$_4$H$_9$O | CHCH$_3$ |
| 267 | 2-n-C$_4$H$_9$O | CHOCH$_3$ |
| 268 | 2-CH(OH)CH$_3$ | NOCH$_3$ |
| 269 | 2-CH(OH)CH$_3$ | CHCH$_3$ |
| 270 | 2-CH(OH)CH$_3$ | CHOCH$_3$ |
| 271 | 2-t-C$_4$H$_9$ | NOCH$_3$ |
| 272 | 2-t-C$_4$H$_9$ | CHCH$_3$ |
| 273 | 2-t-C$_4$H$_9$ | CHOCH$_3$ |
| 274 | 2-s-C$_4$H$_9$ | NOCH$_3$ |
| 275 | 2-s-C$_4$H$_9$ | CHCH$_3$ |
| 276 | 2-s-C$_4$H$_9$ | CHOCH$_3$ |
| 277 | 2-n-C$_3$H$_7$ | NOCH$_3$ |
| 278 | 2-n-C$_3$H$_7$ | CHCH$_3$ |
| 279 | 2-n-C$_3$H$_7$ | CHOCH$_3$ |
| 280 | 2-(E/Z)—CH=CH(CH$_3$) | NOCH$_3$ |
| 281 | 2-(E/Z)—CH=CH(CH$_3$) | CHCH$_3$ |
| 282 | 2-(E/Z)—CH=CH(CH$_3$) | CHOCH$_3$ |
| 283 | 2-Cyano, 5-OCH$_3$ | NOCH$_3$ |
| 284 | 2-Cyano, 5-OCH$_3$ | CHCH$_3$ |
| 285 | 2-Cyano, 5-OCH$_3$ | CHOCH$_3$ |
| 286 | 2-Cyano, 5-N(C$_2$H$_5$)$_2$ | NOCH$_3$ |
| 287 | 2-Cyano, 5-N(C$_2$H$_5$)$_2$ | CHCH$_3$ |
| 288 | 2-Cyano, 5-N(C$_2$H$_5$)$_2$ | CHOCH$_3$ |
| 289 | 2-CONH$_2$ | NOCH$_3$ |
| 290 | 2-CONH$_2$ | CHCH$_3$ |
| 291 | 2-CONH$_2$ | CHOCH$_3$ |
| 292 | 2-C≡CSi(CH$_3$)$_3$ | NOCH$_3$ |
| 293 | 2-C≡CSi(CH$_3$)$_3$ | CHCH$_3$ |
| 294 | 2-C≡CSi(CH$_3$)$_3$ | CHOCH$_3$ |
| 295 | 2-F, 5-F | NOCH$_3$ |
| 296 | 2-F, 5-F | CHCH$_3$ |
| 297 | 2-F, 5-F | CHOCH$_3$ |
| 298 | 2-(E)—CH$_3$OOC—C—CHOCH$_3$ | NOCH$_3$ |
| 299 | 2-(E)—CH$_3$OOC—C—CHOCH$_3$ | CHCH$_3$ |

TABLE C-continued

| No. | R$_x$ | Z |
|---|---|---|
| 300 | 2-(E)—CH$_3$OOC—C—CHOCH$_3$ | CHOCH$_3$ |
| 301 | 3-F, 5-F | NOCH$_3$ |
| 302 | 3-F, 5-F | CHCH$_3$ |
| 303 | 3-F, 5-F | CHOCH$_3$ |
| 304 | 2-NHOH | NOCH$_3$ |
| 305 | 2-NHOH | CHCH$_3$ |
| 306 | 2-NHOH | CHOCH$_3$ |
| 307 | 2-CH$_2$OCH$_3$ | NOCH$_3$ |
| 308 | 2-CH$_2$OCH$_3$ | CHCH$_3$ |
| 309 | 2-CH$_2$OCH$_3$ | CHOCH$_3$ |
| 310 | 2-CH$_2$CN | NOCH$_3$ |
| 311 | 2-CH$_2$CN | CHCH$_3$ |
| 312 | 2-CH$_2$CN | CHOCH$_3$ |
| 313 | 2-N$_3$ | NOCH$_3$ |
| 314 | 2-N$_3$ | CHCH$_3$ |
| 315 | 2-N$_3$ | CHOCH$_3$ |
| 316 | 2-Cyano, 6-F | NOCH$_3$ |
| 317 | 2-Cyano, 6-F | CHCH$_3$ |
| 318 | 2-Cyano, 6-F | CHOCH$_3$ |
| 319 | 2-NO$_2$, 6-F | NOCH$_3$ |
| 320 | 2-NO$_2$, 6-F | CHCH$_3$ |
| 321 | 2-NO$_2$, 6-F | CHOCH$_3$ |
| 322 | 2-CSNH$_2$, 6-F | NOCH$_3$ |
| 323 | 2-CSNH$_2$, 6-F | CHCH$_3$ |
| 324 | 2-CSNH$_2$, 6-F | CHOCH$_3$ |
| 325 | 2-Cyano, 3-F | NOCH$_3$ |
| 326 | 2-Cyano, 3-F | CHCH$_3$ |
| 327 | 2-Cyano, 3-F | CHOCH$_3$ |
| 328 | 2-Cyano, 5-F | NOCH$_3$ |
| 329 | 2-Cyano, 5-F | CHCH$_3$ |
| 330 | 2-Cyano, 5-F | CHOCH$_3$ |
| 331 | 2-Cyano, 3-OCH$_3$ | NOCH$_3$ |
| 332 | 2-Cyano, 3-OCH$_3$ | CHCH$_3$ |
| 333 | 2-Cyano, 3-OCH$_3$ | CHOCH$_3$ |
| 334 | 2-Cyano, 6-OCH$_3$ | NOCH$_3$ |
| 335 | 2-Cyano, 6-OCH$_3$ | CHCH$_3$ |
| 336 | 2-Cyano, 6-OCH$_3$ | CHOCH$_3$ |
| 337 | 2-NO$_2$, 5-OCH$_3$ | NOCH$_3$ |
| 338 | 2-NO$_2$, 5-OCH$_3$ | CHCH$_3$ |
| 339 | 2-NO$_2$, 5-OCH$_3$ | CHOCH$_3$ |
| 340 | 2-NO$_2$, 6-OCH$_3$ | NOCH$_3$ |
| 341 | 2-NO$_2$, 6-OCH$_3$ | CHCH$_3$ |
| 342 | 2-NO$_2$, 6-OCH$_3$ | CHOCH$_3$ |
| 343 | 2-CSNH$_2$, 3-OCH$_3$ | NOCH$_3$ |
| 344 | 2-CSNH$_2$, 3-OCH$_3$ | CHCH$_3$ |
| 345 | 2-CSNH$_2$, 3-OCH$_3$ | CHOCH$_3$ |
| 346 | 2-CSNH$_2$, 5-OCH$_3$ | NOCH$_3$ |
| 347 | 2-CSNH$_2$, 5-OCH$_3$ | CHCH$_3$ |
| 348 | 2-CSNH$_2$, 5-OCH$_3$ | CHOCH$_3$ |
| 349 | 2-CSNH$_2$, 6-OCH$_3$ | NOCH$_3$ |
| 350 | 2-CSNH$_2$, 6-OCH$_3$ | CHCH$_3$ |
| 351 | 2-CSNH$_2$, 6-OCH$_3$ | CHOCH$_3$ |
| 352 | 2-Cyano, 3-cyano | NOCH$_3$ |
| 353 | 2-Cyano, 3-cyano | CHCH$_3$ |
| 354 | 2-Cyano, 3-cyano | CHOCH$_3$ |
| 355 | 2-F, 3-cyano | NOCH$_3$ |
| 356 | 2-F, 3-cyano | CHCH$_3$ |
| 357 | 2-F, 3-cyano | CHOCH$_3$ |
| 358 | 2-OCH$_3$, 3-cyano | NOCH$_3$ |
| 359 | 2-OCH$_3$, 3-cyano | CHCH$_3$ |
| 360 | 2-OCH$_3$, 3-cyano | CHOCH$_3$ |
| 361 | 3-Cyano, 6-F | NOCH$_3$ |
| 362 | 3-Cyano, 6-F | CHCH$_3$ |
| 363 | 3-Cyano, 6-F | CHOCH$_3$ |
| 364 | 2-Cyano, 6-Br | NOCH$_3$ |
| 365 | 2-Cyano, 6-Br | CHCH$_3$ |
| 366 | 2-Cyano, 6-Br | CHOCH$_3$ |
| 367 | 2-Cyano, 6-NO$_2$ | NOCH$_3$ |
| 368 | 2-Cyano, 6-NO$_2$ | CHCH$_3$ |
| 369 | 2-Cyano, 6-NO$_2$ | CHOCH$_3$ |
| 370 | 2-Cyano, 6-OC$_2$H$_5$ | NOCH$_3$ |
| 371 | 2-Cyano, 6-OC$_2$H$_5$ | CHCH$_3$ |
| 372 | 2-Cyano, 6-OC$_2$H$_5$ | CHOCH$_3$ |
| 373 | 2-Cyano, 6-CO$_2$C$_2$H$_5$ | NOCH$_3$ |
| 374 | 2-Cyano, 6-CO$_2$C$_2$H$_5$ | CHCH$_3$ |
| 375 | 2-Cyano, 6-CO$_2$C$_2$H$_5$ | CHOCH$_3$ |
| 376 | 2-Cyano, 6-CH$_3$ | NOCH$_3$ |
| 377 | 2-Cyano, 6-CH$_3$ | CHCH$_3$ |
| 378 | 2-Cyano, 6-CH$_3$ | CHOCH$_3$ |
| 379 | 2-Cyano, 5-CH$_2$C$_6$H$_5$ | NOCH$_3$ |
| 380 | 2-Cyano, 5-CH$_2$C$_6$H$_5$ | CHCH$_3$ |
| 381 | 2-Cyano, 5-CH$_2$C$_6$H$_5$ | CHOCH$_3$ |
| 382 | 2-COOH | NOCH$_3$ |
| 383 | 2-COOH | CHCH$_3$ |
| 384 | 2-COOH | CHOCH$_3$ |
| 385 | 2-C(CH$_3$)=NOCH$_3$ | NOCH$_3$ |
| 386 | 2-C(CH$_3$)=NOCH$_3$ | CHCH$_3$ |
| 387 | 2-C(CH$_3$)=NOCH$_3$ | CHOCH$_3$ |
| 388 | 4-OH | NOCH$_3$ |
| 389 | 4-OCH$_3$ | NOCH$_3$ |
| 390 | 4-OC$_6$H$_5$ | NOCH$_3$ |
| 391 | 4-Cyano | NOCH$_3$ |
| 392 | 4-CHO | NOCH$_3$ |
| 393 | 4-(E)—CH=NOH | NOCH$_3$ |
| 394 | 4-(E)—CH=NOCH$_3$ | NOCH$_3$ |
| 395 | 4-(E)—C(CH$_3$)=NOCH$_3$ | NOCH$_3$ |
| 396 | 4-SCN | NOCH$_3$ |
| 397 | 4-SCH$_3$ | NOCH$_3$ |
| 398 | 4-SO$_2$(CH$_2$)$_3$CH$_3$ | NOCH$_3$ |
| 399 | 4-NO$_2$ | NOCH$_3$ |
| 400 | 2-F, 4-F | NOCH$_3$ |
| 401 | 2-Cl, 4-Cl | NOCH$_3$ |
| 402 | 2-NO$_2$, 4-F | NOCH$_3$ |
| 403 | 2-CN, 4-Cl | NOCH$_3$ |
| 404 | 2-CN, 4-Br | NOCH$_3$ |
| 405 | 2-CN, 4-NO$_2$ | NOCH$_3$ |
| 406 | 2-CN, 4-OCH$_3$ | NOCH$_3$ |
| 407 | 2-CN, 4-OCF$_3$ | NOCH$_3$ |
| 408 | 2-CN, 4-CN | NOCH$_3$ |
| 409 | 2-CN, 4-COOCH$_3$ | NOCH$_3$ |
| 410 | 3-CN, 4-F | NOCH$_3$ |
| 411 | 2-CSNH$_2$, 4-OCH$_3$ | NOCH$_3$ |
| 412 | 2-NO$_2$, 4-OCH$_3$ | NOCH$_3$ |

TABLE D

"Pos" indicates the position in the pyridine ring which is substituted by the pyrimidinyl radical (for numbering see formula).

| No. | R$_x$ | Pos | Z |
|---|---|---|---|
| 1 | 3-F | 2 | NOCH$_3$ |
| 2 | 3-F | 2 | CHCH$_3$ |
| 3 | 3-F | 2 | CHOCH$_3$ |
| 4 | 3-Cl | 2 | NOCH$_3$ |
| 5 | 3-Cl | 2 | CHCH$_3$ |
| 6 | 3-Cl | 2 | CHOCH$_3$ |
| 7 | 3-Br | 2 | NOCH$_3$ |
| 8 | 3-Br | 2 | CHCH$_3$ |
| 9 | 3-Br | 2 | CHOCH$_3$ |
| 10 | 3-CH$_3$ | 2 | NOCH$_3$ |
| 11 | 3-CH$_3$ | 2 | CHCH$_3$ |
| 12 | 3-CH$_3$ | 2 | CHOCH$_3$ |
| 13 | 3-OCH$_3$ | 2 | NOCH$_3$ |
| 14 | 3-OCH$_3$ | 2 | CHCH$_3$ |
| 15 | 3-OCH$_3$ | 2 | CHOCH$_3$ |
| 16 | 3-CN | 2 | NOCH$_3$ |
| 17 | 3-CN | 2 | CHCH$_3$ |
| 18 | 3-CN | 2 | CHOCH$_3$ |
| 19 | 3-NO$_2$ | 2 | NOCH$_3$ |
| 20 | 3-NO$_2$ | 2 | CHCH$_3$ |
| 21 | 3-NO$_2$ | 2 | CHOCH$_3$ |
| 22 | 3-OH | 2 | NOCH$_3$ |
| 23 | 3-OH | 2 | CHCH$_3$ |
| 24 | 3-OH | 2 | CHOCH$_3$ |
| 25 | 3-NH$_2$ | 2 | NOCH$_3$ |
| 26 | 3-NH$_2$ | 2 | CHCH$_3$ |
| 27 | 3-NH$_2$ | 2 | CHOCH$_3$ |
| 28 | 3-SCH$_3$ | 2 | NOCH$_3$ |
| 29 | 3-SCH$_3$ | 2 | CHCH$_3$ |

TABLE D-continued

"Pos" indicates the position in the pyridine ring which is substituted by the pyrimidinyl radical (for numbering see formula).

| No. | $R_x$ | Pos | Z |
|---|---|---|---|
| 30 | 3-SCH$_3$ | 2 | CHOCH$_3$ |
| 31 | 3-SO$_2$CH$_3$ | 2 | NOCH$_3$ |
| 32 | 3-SO$_2$CH$_3$ | 2 | CHCH$_3$ |
| 33 | 3-SO$_2$CH$_3$ | 2 | CHOCH$_3$ |
| 34 | 4-CH$_3$ | 2 | NOCH$_3$ |
| 35 | 4-CH$_3$ | 2 | CHCH$_3$ |
| 36 | 4-CH$_3$ | 2 | CHOCH$_3$ |
| 37 | 4-CF$_3$ | 2 | NOCH$_3$ |
| 38 | 4-CF$_3$ | 2 | CHCH$_3$ |
| 39 | 4-CF$_3$ | 2 | CHOCH$_3$ |
| 40 | 5-Cl | 2 | NOCH$_3$ |
| 41 | 5-Cl | 2 | CHCH$_3$ |
| 42 | 5-Cl | 2 | CHOCH$_3$ |
| 43 | 5-Br | 2 | NOCH$_3$ |
| 44 | 5-Br | 2 | CHCH$_3$ |
| 45 | 5-Br | 2 | CHOCH$_3$ |
| 46 | 5-CF$_3$ | 2 | NOCH$_3$ |
| 47 | 5-CF$_3$ | 2 | CHCH$_3$ |
| 48 | 5-CF$_3$ | 2 | CHOCH$_3$ |
| 49 | 5-CH$_3$ | 2 | NOCH$_3$ |
| 50 | 5-CH$_3$ | 2 | CHCH$_3$ |
| 51 | 5-CH$_3$ | 2 | CHOCH$_3$ |
| 52 | 5-CSNH$_2$ | 2 | NOCH$_3$ |
| 53 | 5-CSNH$_2$ | 2 | CHCH$_3$ |
| 54 | 5-CSNH$_2$ | 2 | CHOCH$_3$ |
| 55 | 1-O (ie. N-oxide) | 2 | NOCH$_3$ |
| 56 | 1-O (ie. N-oxide) | 2 | CHCH$_3$ |
| 57 | 1-O (ie. N-oxide) | 2 | CHOCH$_3$ |
| 58 | 5-F | 3 | NOCH$_3$ |
| 59 | 5-F | 3 | CHCH$_3$ |
| 60 | 5-F | 3 | CHOCH$_3$ |
| 61 | 6-F | 3 | NOCH$_3$ |
| 62 | 6-F | 3 | CHCH$_3$ |
| 63 | 6-F | 3 | CHOCH$_3$ |
| 64 | 5-Cl | 3 | NOCH$_3$ |
| 65 | 5-Cl | 3 | CHCH$_3$ |
| 66 | 5-Cl | 3 | CHOCH$_3$ |
| 67 | 6-Cl | 3 | NOCH$_3$ |
| 68 | 6-Cl | 3 | CHCH$_3$ |
| 69 | 6-Cl | 3 | CHOCH$_3$ |
| 70 | 5-CN | 3 | NOCH$_3$ |
| 71 | 5-CN | 3 | CHCH$_3$ |
| 72 | 5-CN | 3 | CHOCH$_3$ |
| 73 | 6-CN | 3 | NOCH$_3$ |
| 74 | 6-CN | 3 | CHCH$_3$ |
| 75 | 6-CN | 3 | CHOCH$_3$ |
| 76 | 5-NO$_2$ | 3 | NOCH$_3$ |
| 77 | 5-NO$_2$ | 3 | CHCH$_3$ |
| 78 | 5-NO$_2$ | 3 | CHOCH$_3$ |
| 79 | 6-NO$_2$ | 3 | NOCH$_3$ |
| 80 | 6-NO$_2$ | 3 | CHCH$_3$ |
| 81 | 6-NO$_2$ | 3 | CHOCH$_3$ |
| 82 | 5-NH(CH$_3$) | 3 | NOCH$_3$ |
| 83 | 5-NH(CH$_3$) | 3 | CHCH$_3$ |
| 84 | 5-NH(CH$_3$) | 3 | CHOCH$_3$ |
| 85 | 5-NH—CONH(C$_2$H$_5$) | 3 | NOCH$_3$ |
| 86 | 5-NH—CONH(C$_2$H$_5$) | 3 | CHCH$_3$ |
| 87 | 5-NH—CONH(C$_2$H$_5$) | 3 | CHOCH$_3$ |
| 88 | 5-NH—SO$_2$C$_6$H$_5$ | 3 | NOCH$_3$ |
| 89 | 5-NH—SO$_2$C$_6$H$_5$ | 3 | CHCH$_3$ |
| 90 | 5-NH—SO$_2$C$_6$H$_5$ | 3 | CHOCH$_3$ |
| 91 | 5-OH | 3 | NOCH$_3$ |
| 92 | 5-OH | 3 | CHCH$_3$ |
| 93 | 5-OH | 3 | CHOCH$_3$ |
| 94 | 6-OH | 3 | NOCH$_3$ |
| 95 | 6-OH | 3 | CHCH$_3$ |
| 96 | 6-OH | 3 | CHOCH$_3$ |
| 97 | 5-OCH$_3$ | 3 | NOCH$_3$ |
| 98 | 5-OCH$_3$ | 3 | CHCH$_3$ |
| 99 | 5-OCH$_3$ | 3 | CHOCH$_3$ |
| 100 | 6-OCH$_3$ | 3 | NOCH$_3$ |
| 101 | 6-OCH$_3$ | 3 | CHCH$_3$ |
| 102 | 6-OCH$_3$ | 3 | CHOCH$_3$ |
| 103 | 5-O(2-F—C$_6$H$_4$) | 3 | NOCH$_3$ |
| 104 | 5-O(2-F—C$_6$H$_4$) | 3 | CHCH$_3$ |
| 105 | 5-O(2-F—C$_6$H$_4$) | 3 | CHOCH$_3$ |
| 106 | 5-OSO$_2$(4-CH$_3$—C$_6$H$_4$) | 3 | NOCH$_3$ |
| 107 | 5-OSO$_2$(4-CH$_3$—C$_6$H$_4$) | 3 | CHCH$_3$ |
| 108 | 5-OSO$_2$(4-CH$_3$—C$_6$H$_4$) | 3 | CHOCH$_3$ |
| 109 | 5-SCN | 3 | NOCH$_3$ |
| 110 | 5-SCN | 3 | CHCH$_3$ |
| 111 | 5-SCN | 3 | CHOCH$_3$ |
| 112 | 6-SCN | 3 | NOCH$_3$ |
| 113 | 6-SCN | 3 | CHCH$_3$ |
| 114 | 6-SCN | 3 | CHOCH$_3$ |
| 115 | 5-SCH$_3$ | 3 | NOCH$_3$ |
| 116 | 5-SCH$_3$ | 3 | CHCH$_3$ |
| 117 | 5-SCH$_3$ | 3 | CHOCH$_3$ |
| 118 | 6-SCH$_3$ | 3 | NOCH$_3$ |
| 119 | 6-SCH$_3$ | 3 | CHCH$_3$ |
| 120 | 6-SCH$_3$ | 3 | CHOCH$_3$ |
| 121 | 6-SO$_2$(CH$_2$)$_3$CH$_3$ | 3 | NOCH$_3$ |
| 122 | 6-SO$_2$(CH$_2$)$_3$CH$_3$ | 3 | CHCH$_3$ |
| 123 | 6-SO$_2$(CH$_2$)$_3$CH$_3$ | 3 | CHOCH$_3$ |
| 124 | 5-CHO | 3 | NOCH$_3$ |
| 125 | 5-CHO | 3 | CHCH$_3$ |
| 126 | 5-CHO | 3 | CHOCH$_3$ |
| 127 | 6-CHO | 3 | NOCH$_3$ |
| 128 | 6-CHO | 3 | CHCH$_3$ |
| 129 | 6-CHO | 3 | CHOCH$_3$ |
| 130 | 5-COC$_6$H$_5$ | 3 | NOCH$_3$ |
| 131 | 5-COC$_6$H$_5$ | 3 | CHCH$_3$ |
| 132 | 5-COC$_6$H$_5$ | 3 | CHOCH$_3$ |
| 133 | 5-(E)—CH=NOH | 3 | NOCH$_3$ |
| 134 | 5-(E)—CH=NOH | 3 | CHCH$_3$ |
| 135 | 5-(E)—CH=NOH | 3 | CHOCH$_3$ |
| 136 | 6-(E)—CH=NOH | 3 | NOCH$_3$ |
| 137 | 6-(E)—CH=NOH | 3 | CHCH$_3$ |
| 138 | 6-(E)—CH=NOH | 3 | CHOCH$_3$ |
| 139 | 5-CONH(CH)$_3$ | 3 | NOCH$_3$ |
| 140 | 5-CONH(CH)$_3$ | 3 | CHCH$_3$ |
| 141 | 5-CONH(CH)$_3$ | 3 | CHOCH$_3$ |
| 142 | 6-CONH(CH)$_3$ | 3 | NOCH$_3$ |
| 143 | 6-CONH(CH)$_3$ | 3 | CHCH$_3$ |
| 144 | 6-CONH(CH)$_3$ | 3 | CHOCH$_3$ |
| 145 | 5-CH$_3$ | 3 | NOCH$_3$ |
| 146 | 5-CH$_3$ | 3 | CHCH$_3$ |
| 147 | 5-CH$_3$ | 3 | CHOCH$_3$ |
| 148 | 6-CH$_3$ | 3 | NOCH$_3$ |
| 149 | 6-CH$_3$ | 3 | CHCH$_3$ |
| 150 | 6-CH$_3$ | 3 | CHOCH$_3$ |
| 151 | 5-CH$_2$CN | 3 | NOCH$_3$ |
| 152 | 5-CH$_2$CN | 3 | CHCH$_3$ |
| 153 | 5-CH$_2$CN | 3 | CHOCH$_3$ |
| 154 | 6-CH$_2$CN | 3 | NOCH$_3$ |
| 155 | 6-CH$_2$CN | 3 | CHCH$_3$ |
| 156 | 6-CH$_2$CN | 3 | CHOCH$_3$ |
| 157 | 5-CH$_2$OCH$_3$ | 3 | NOCH$_3$ |
| 158 | 5-CH$_2$OCH$_3$ | 3 | CHCH$_3$ |
| 159 | 5-CH$_2$OCH$_3$ | 3 | CHOCH$_3$ |
| 160 | 5-CH$_2$C(CH$_3$)=CH$_2$ | 3 | NOCH$_3$ |
| 161 | 5-CH$_2$C(CH$_3$)=CH$_2$ | 3 | CHCH$_3$ |
| 162 | 5-CH$_2$C(CH$_3$)=CH$_2$ | 3 | CHOCH$_3$ |
| 163 | 5-C$_6$H$_5$ | 3 | NOCH$_3$ |
| 164 | 5-C$_6$H$_5$ | 3 | CHCH$_3$ |
| 165 | 5-C$_6$H$_5$ | 3 | CHOCH$_3$ |
| 166 | 6-C$_6$H$_5$ | 3 | NOCH$_3$ |
| 167 | 6-C$_6$H$_5$ | 3 | CHCH$_3$ |
| 168 | 6-C$_6$H$_5$ | 3 | CHOCH$_3$ |
| 169 | 5-OC$_6$H$_5$ | 3 | NOCH$_3$ |
| 170 | 5-OC$_6$H$_5$ | 3 | CHCH$_3$ |
| 171 | 5-OC$_6$H$_5$ | 3 | CHOCH$_3$ |
| 172 | 6-OC$_6$H$_5$ | 3 | NOCH$_3$ |
| 173 | 6-OC$_6$H$_5$ | 3 | CHCH$_3$ |
| 174 | 6-OC$_6$H$_5$ | 3 | CHOCH$_3$ |
| 175 | 5-OCH$_3$, 6-CH$_3$ | 3 | NOCH$_3$ |
| 176 | 5-OCH$_3$, 6-CH$_3$ | 3 | CHCH$_3$ |
| 177 | 5-OCH$_3$, 6-CH$_3$ | 3 | CHOCH$_3$ |

TABLE D-continued

"Pos" indicates the position in the pyridine ring which is substituted by the pyrimidinyl radical (for numbering see formula).

| No. | $R_x$ | Pos | Z |
|---|---|---|---|
| 178 | 5-CN, 6-F | 3 | $NOCH_3$ |
| 179 | 5-CN, 6-F | 3 | $CHCH_3$ |
| 180 | 5-CN, 6-F | 3 | $CHOCH_3$ |
| 181 | 5-$OCH_3$, 6-CN | 3 | $NOCH_3$ |
| 182 | 5-$OCH_3$, 6-CN | 3 | $CHCH_3$ |
| 183 | 5-$OCH_3$, 6-CN | 3 | $CHOCH_3$ |
| 184 | 4-F | 3 | $NOCH_3$ |
| 185 | 4-F | 3 | $CHCH_3$ |
| 186 | 4-F | 3 | $CHOCH_3$ |
| 187 | 4-Cl | 3 | $NOCH_3$ |
| 188 | 4-Cl | 3 | $CHCH_3$ |
| 189 | 4-Cl | 3 | $CHOCH_3$ |
| 190 | 4-Br | 3 | $NOCH_3$ |
| 191 | 4-Br | 3 | $CHCH_3$ |
| 192 | 4-Br | 3 | $CHOCH_3$ |
| 193 | 4-CN | 3 | $NOCH_3$ |
| 194 | 4-CN | 3 | $CHCH_3$ |
| 195 | 4-CN | 3 | $CHOCH_3$ |
| 196 | 4-$NO_2$ | 3 | $NOCH_3$ |
| 197 | 4-$NO_2$ | 3 | $CHCH_3$ |
| 198 | 4-$NO_2$ | 3 | $CHOCH_3$ |
| 199 | 4-$NH_2$ | 3 | $NOCH_3$ |
| 200 | 4-$NH_2$ | 3 | $CHCH_3$ |
| 201 | 4-$NH_2$ | 3 | $CHOCH_3$ |
| 202 | 4-N—$(CH_3)_2$ | 3 | $NOCH_3$ |
| 203 | 4-N—$(CH_3)_2$ | 3 | $CHCH_3$ |
| 204 | 4-N—$(CH_3)_2$ | 3 | $CHOCH_3$ |
| 205 | 4-NH—CHO | 3 | $NOCH_3$ |
| 206 | 4-NH—CHO | 3 | $CHCH_3$ |
| 207 | 4-NH—CHO | 3 | $CHOCH_3$ |
| 208 | 4-NH—$CONH_2$ | 3 | $NOCH_3$ |
| 209 | 4-NH—$CONH_2$ | 3 | $CHCH_3$ |
| 210 | 4-NH—$CONH_2$ | 3 | $CHOCH_3$ |
| 211 | 4-NH—$SO_2CH_3$ | 3 | $NOCH_3$ |
| 212 | 4-NH—$SO_2CH_3$ | 3 | $CHCH_3$ |
| 213 | 4-NH—$SO_2CH_3$ | 3 | $CHOCH_3$ |
| 214 | 4-OH | 3 | $NOCH_3$ |
| 215 | 4-OH | 3 | $CHCH_3$ |
| 216 | 4-OH | 3 | $CHOCH_3$ |
| 217 | 4-$OCH_3$ | 3 | $NOCH_3$ |
| 218 | 4-$OCH_3$ | 3 | $CHCH_3$ |
| 219 | 4-$OCH_3$ | 3 | $CHOCH_3$ |
| 220 | 4-$OCOCH_3$ | 3 | $NOCH_3$ |
| 221 | 4-$OCOCH_3$ | 3 | $CHCH_3$ |
| 222 | 4-$OCOCH_3$ | 3 | $CHOCH_3$ |
| 223 | 4-$OSO_2CH_3$ | 3 | $NOCH_3$ |
| 224 | 4-$OSO_2CH_3$ | 3 | $CHCH_3$ |
| 225 | 4-$OSO_2CH_3$ | 3 | $CHOCH_3$ |
| 226 | 4-SCN | 3 | $NOCH_3$ |
| 227 | 4-SCN | 3 | $CHCH_3$ |
| 228 | 4-SCN | 3 | $CHOCH_3$ |
| 229 | 4-$SCH_3$ | 3 | $NOCH_3$ |
| 230 | 4-$SCH_3$ | 3 | $CHCH_3$ |
| 231 | 4-$SCH_3$ | 3 | $CHOCH_3$ |
| 232 | 4-S—$(O)CH_3$ | 3 | $NOCH_3$ |
| 233 | 4-S—$(O)CH_3$ | 3 | $CHCH_3$ |
| 234 | 4-S—$(O)CH_3$ | 3 | $CHOCH_3$ |
| 235 | 4-$SO_2CH_3$ | 3 | $NOCH_3$ |
| 236 | 4-$SO_2CH_3$ | 3 | $CHCH_3$ |
| 237 | 4-$SO_2CH_3$ | 3 | $CHOCH_3$ |
| 238 | 4-CHO | 3 | $NOCH_3$ |
| 289 | 4-CHO | 3 | $CHCH_3$ |
| 240 | 4-CHO | 3 | $CHOCH_3$ |
| 241 | 4-$COCH_3$ | 3 | $NOCH_3$ |
| 242 | 4-$COCH_3$ | 3 | $CHCH_3$ |
| 243 | 4-$COCH_3$ | 3 | $CHOCH_3$ |
| 244 | 4-(E)—CH=NOH | 3 | $NOCH_3$ |
| 245 | 4-(E)—CH=NOH | 3 | $CHCH_3$ |
| 246 | 4-(E)—CH=NOH | 3 | $CHOCH_3$ |
| 247 | 4-$CONH_2$ | 3 | $NOCH_3$ |
| 248 | 4-$CONH_2$ | 3 | $CHCH_3$ |
| 249 | 4-$CONH_2$ | 3 | $CHOCH_3$ |
| 250 | 4-$CH_3$ | 3 | $NOCH_3$ |
| 251 | 4-$CH_3$ | 3 | $CHCH_3$ |
| 252 | 4-$CH_3$ | 3 | $CHOCH_3$ |
| 253 | 4-$CH_2Br$ | 3 | $NOCH_3$ |
| 254 | 4-$CH_2Br$ | 3 | $CHCH_3$ |
| 255 | 4-$CH_2Br$ | 3 | $CHOCH_3$ |
| 256 | 4-$CF_3$ | 3 | $NOCH_3$ |
| 257 | 4-$CF_3$ | 3 | $CHCH_3$ |
| 258 | 4-$CF_3$ | 3 | $CHOCH_3$ |
| 259 | 4-$CH_2CN$ | 3 | $NOCH_3$ |
| 260 | 4-$CH_2CN$ | 3 | $CHCH_3$ |
| 261 | 4-$CH_2CN$ | 3 | $CHOCH_3$ |
| 262 | 4-$CH_2OCH_3$ | 3 | $NOCH_3$ |
| 263 | 4-$CH_2OCH_3$ | 3 | $CHCH_3$ |
| 264 | 4-$CH_2OCH_3$ | 3 | $CHOCH_3$ |
| 265 | 4-$CH_2CH=CH_2$ | 3 | $NOCH_3$ |
| 266 | 4-$CH_2CH=CH_2$ | 3 | $CHCH_3$ |
| 267 | 4-$CH_2CH=CH_2$ | 3 | $CHOCH_3$ |
| 268 | 4-$OCH_2CH=CH_2$ | 3 | $NOCH_3$ |
| 269 | 4-$OCH_2CH=CH_2$ | 3 | $CHCH_3$ |
| 270 | 4-$OCH_2CH=CH_2$ | 3 | $CHOCH_3$ |
| 271 | 4-$C_6H_5$ | 3 | $NOCH_3$ |
| 272 | 4-$C_6H_5$ | 3 | $CHCH_3$ |
| 273 | 4-$C_6H_5$ | 3 | $CHOCH_3$ |
| 274 | 4-$OC_6H_5$ | 3 | $NOCH_3$ |
| 275 | 4-$OC_6H_5$ | 3 | $CHCH_3$ |
| 276 | 4-$OC_6H_5$ | 3 | $CHOCH_3$ |
| 277 | 1-$O^-$(ie. N-oxide) | 3 | $NOCH_3$ |
| 278 | 1-$O^-$(ie. N-oxide) | 3 | $CHCH_3$ |
| 279 | 1-$O^-$(ie. N-oxide) | 3 | $CHOCH_3$ |
| 280 | 4-$CSNH_4$ | 3 | $NOCH_3$ |
| 281 | 4-$CSNH_4$ | 3 | $CHCH_3$ |
| 282 | 4-$CSNH_4$ | 3 | $CHOCH_3$ |
| 283 | 3-F | 4 | $NOCH_3$ |
| 284 | 3-F | 4 | $CHCH_3$ |
| 285 | 3-F | 4 | $CHOCH_3$ |
| 286 | 3-Cl | 4 | $NOCH_3$ |
| 287 | 3-Cl | 4 | $CHCH_3$ |
| 288 | 3-Cl | 4 | $CHOCH_3$ |
| 289 | 3-Br | 4 | $NOCH_3$ |
| 290 | 3-Br | 4 | $CHCH_3$ |
| 291 | 3-Br | 4 | $CHOCH_3$ |
| 292 | 3-$CF_3$ | 4 | $NOCH_3$ |
| 293 | 3-$CF_3$ | 4 | $CHCH_3$ |
| 294 | 3-$CF_3$ | 4 | $CHOCH_3$ |
| 295 | 3-$CH_3$ | 4 | $NOCH_3$ |
| 296 | 3-$CH_3$ | 4 | $CHCH_3$ |
| 297 | 3-$CH_3$ | 4 | $CHOCH_3$ |
| 298 | 3-$OCH_3$ | 4 | $NOCH_3$ |
| 299 | 3-$OCH_3$ | 4 | $CHCH_3$ |
| 300 | 3-$OCH_3$ | 4 | $CHOCH_3$ |
| 301 | 3-$SCH_3$ | 4 | $NOCH_3$ |
| 302 | 3-$SCH_3$ | 4 | $CHCH_3$ |
| 303 | 3-$SCH_3$ | 4 | $CHOCH_3$ |
| 304 | 3-CN | 4 | $NOCH_3$ |
| 305 | 3-CN | 4 | $CHCH_3$ |
| 306 | 3-CN | 4 | $CHOCH_3$ |
| 307 | 3-$NO_2$ | 4 | $NOCH_3$ |
| 308 | 3-$NO_2$ | 4 | $CHCH_3$ |
| 309 | 3-$NO_2$ | 4 | $CHOCH_3$ |
| 310 | 3-$N(CH_3)_2$ | 4 | $NOCH_3$ |
| 311 | 3-$N(CH_3)_2$ | 4 | $CHCH_3$ |
| 312 | 3-$N(CH_3)_2$ | 4 | $CHOCH_3$ |
| 313 | 2-F | 4 | $NOCH_3$ |
| 314 | 2-F | 4 | $CHCH_3$ |
| 315 | 2-F | 4 | $CHOCH_3$ |
| 316 | 2-Cl | 4 | $NOCH_3$ |
| 317 | 2-Cl | 4 | $CHCH_3$ |
| 318 | 2-Cl | 4 | $CHOCH_3$ |
| 319 | 2-Br | 4 | $NOCH_3$ |
| 320 | 2-Br | 4 | $CHCH_3$ |
| 321 | 2-Br | 4 | $CHOCH_3$ |
| 322 | 2-$CF_3$ | 4 | $NOCH_3$ |
| 323 | 2-$CF_3$ | 4 | $CHCH_3$ |
| 324 | 2-$CF_3$ | 4 | $CHOCH_3$ |
| 325 | 2-$CH_3$ | 4 | $NOCH_3$ |

TABLE D-continued

"Pos" indicates the position in the pyridine ring which is substituted by the pyrimidinyl radical (for numbering see formula).

| No. | $R_x$ | Pos | Z |
|---|---|---|---|
| 326 | 2-CH$_3$ | 4 | CHCH$_3$ |
| 327 | 2-CH$_3$ | 4 | CHOCH$_3$ |
| 328 | 2-OCH$_3$ | 4 | NOCH$_3$ |
| 329 | 2-OCH$_3$ | 4 | CHCH$_3$ |
| 330 | 2-OCH$_3$ | 4 | CHOCH$_3$ |
| 331 | 2-SCH$_3$ | 4 | NOCH$_3$ |
| 332 | 2-CH$_3$ | 4 | CHCH$_3$ |
| 333 | 2-SCH$_3$ | 4 | CHOCH$_3$ |
| 334 | 2-CN | 4 | NOCH$_3$ |
| 335 | 2-CN | 4 | CHCH$_3$ |
| 336 | 2-CN | 4 | CHOCH$_3$ |
| 337 | 2-NO$_2$ | 4 | NOCH$_3$ |
| 338 | 2-NO$_2$ | 4 | CHCH$_3$ |
| 339 | 2-NO$_2$ | 4 | CHOCH$_3$ |
| 340 | 3-CN, 2-F | 4 | NOCH$_3$ |
| 341 | 3-CN, 2-F | 4 | CHCH$_3$ |
| 342 | 3-CN, 2-F | 4 | CHOCH$_3$ |
| 343 | 3-F, 5-F | 4 | NOCH$_3$ |
| 344 | 3-F, 5-F | 4 | CHCH$_3$ |
| 345 | 3-F, 5-F | 4 | CHOCH$_3$ |
| 346 | 6-Br | 2 | NOCH$_3$ |
| 347 | 6-CH$_3$ | 2 | NOCH$_3$ |
| 348 | 2-F | 3 | NOCH$_3$ |
| 349 | 2-Cl | 3 | NOCH$_3$ |
| 350 | 2-Br | 3 | NOCH$_3$ |
| 351 | 2-CN | 3 | NOCH$_3$ |
| 352 | 2-NC | 3 | NOCH$_3$ |
| 353 | 2-NO$_2$ | 3 | NOCH$_3$ |
| 354 | 2-NH$_2$ | 3 | NOCH$_3$ |
| 355 | 2-N(CH$_3$)$_2$ | 3 | NOCH$_3$ |
| 356 | 2-NHCHO | 3 | NOCH$_3$ |
| 357 | 2-NHCOCH$_3$ | 3 | NOCH$_3$ |
| 358 | 2-NHCOC$_6$H$_5$ | 3 | NOCH$_3$ |
| 359 | 2-NHCONH$_2$ | 3 | NOCH$_3$ |
| 360 | 2-NHSO$_2$CH$_3$ | 3 | NOCH$_3$ |
| 361 | 2-OH | 3 | NOCH$_3$ |
| 362 | 2-OCH$_3$ | 3 | NOCH$_3$ |
| 363 | 2-OCOCH$_3$ | 3 | NOCH$_3$ |
| 364 | 2-OSO$_2$CH$_3$ | 3 | NOCH$_3$ |
| 365 | 2-OC$_2$H$_5$ | 3 | NOCH$_3$ |
| 366 | 2-SCH$_3$ | 3 | NOCH$_3$ |
| 367 | 2-S(O)CH$_3$ | 3 | NOCH$_3$ |
| 368 | 2-SCN | 3 | NOCH$_3$ |
| 369 | 2-SO$_2$CH$_3$ | 3 | NOCH$_3$ |
| 370 | 2-CHO | 3 | NOCH$_3$ |
| 371 | 2-COCH$_3$ | 3 | NOCH$_3$ |
| 372 | 2-(E)—CH=NOH | 3 | NOCH$_3$ |
| 373 | 2-(E)—CH=NOCH$_3$ | 3 | NOCH$_3$ |
| 374 | 2-(E)—C(CH$_3$)=NOH | 3 | NOCH$_3$ |
| 375 | 2-(E)—C(CH$_3$)=NOCH$_3$ | 3 | NOCH$_3$ |
| 376 | 2-CONH$_2$ | 3 | NOCH$_3$ |
| 377 | 2-CSNH$_2$ | 3 | NOCH$_3$ |
| 378 | 2-CSNHCH$_3$ | 3 | NOCH$_3$ |
| 379 | 2-C$_2$H$_5$ | 3 | NOCH$_3$ |
| 380 | 2-CH$_2$F | 3 | NOCH$_3$ |
| 381 | 2-CH$_2$Cl | 3 | NOCH$_3$ |
| 382 | 2-CH$_2$Br | 3 | NOCH$_3$ |
| 383 | 2-CH$_2$CN | 3 | NOCH$_3$ |
| 384 | 2-CH$_2$CN | 3 | NOCH$_3$ |
| 385 | 2-CH$_2$OCH$_3$ | 3 | NOCH$_3$ |
| 386 | 2-CH$_2$OCOCH$_3$ | 3 | NOCH$_3$ |
| 387 | 2-CH=CH$_2$ | 3 | NOCH$_3$ |
| 388 | 2-C≡CH | 3 | NOCH$_3$ |
| 389 | 2-CH$_2$C≡CCH$_3$ | 3 | NOCH$_3$ |
| 390 | 2-OCH$_2$CH=CHCH$_3$ | 3 | NOCH$_3$ |
| 391 | 2-C$_6$H$_5$ | 3 | NOCH$_3$ |
| 392 | 2-OC$_6$H$_5$ | 3 | NOCH$_3$ |
| 393 | 2-(4-Cl—OC$_6$H$_4$) | 3 | NOCH$_3$ |
| 394 | 2-OCH$_2$C$_6$H$_5$ | 3 | NOCH$_3$ |
| 395 | 2-CN | 3 | NOCH$_3$ |
| 396 | 2-NO$_2$ | 3 | NOCH$_3$ |
| 397 | 2-Cl | 3 | NOCH$_3$ |
| 398 | 2-OCH$_3$ | 3 | NOCH$_3$ |
| 399 | 2-CN | 3 | NOCH$_3$ |
| 400 | 5-Cl | 3 | NOCH$_3$ |
| 401 | 2-CN | 3 | NOCH$_3$ |
| 402 | 2-F | 3 | NOCH$_3$ |
| 403 | 2-F | 3 | NOCH$_3$ |
| 404 | 2-NO$_2$ | 3 | NOCH$_3$ |
| 405 | H | 2 | NOCH$_3$ |
| 406 | 6-Cl | 2 | NOCH$_3$ |
| 407 | H | 3 | NOCH$_3$ |
| 408 | 2-CH$_3$ | 3 | NOCH$_3$ |
| 409 | H | 4 | NOCH$_3$ |

As a result of the preparation, the naphthyl ethers of the formula I can be obtained as E/Z isomer mixtures on account of the C=C or C=N double bonds. The isomeric compounds can be separated into the isomerically pure compounds in a customary manner by crystallization or chromatography. Both the isomer mixtures and the isomerically pure compounds can be used in the manner according to the invention for the control of animal pests and harmful fungi.

The compounds I are distinguished by an outstanding activity against a broad spectrum of phytopathogenic fungi, in particular from the Ascomycetes and Basidiomycetes classes. They are systemically active in some cases and can be employed as foliar and soil fungicides.

They are of particular importance for the control of a multiplicity of fungi on various crop plants such as wheat, rye, barley, oats, rice, corn, grass, cotton, soybeans, coffee, sugar cane, grapes, fruit and decorative plants and vegetable plants such as cucumbers, beans and Cucurbitaceae, and on the seeds of these plants.

They are specifically suitable for the control of the following plant diseases:

*Erysiphe graminis* (powdery mildew) in cereals, *Erysiphe cichoracearum* and *Sphaerotheca fuliginea* on Cucurbitaceae, *Podosphaera leucotricha* on apples, *Uncinula necator* on vines, Puccinia species on cereals, *Rhizoctonia* species on cotton and lawns, Ustilago species on cereals and sugar cane, *Venturia inaequalis* (scab) on apples, *Helminthosporium* species on cereals, *Septoria nodorum* on wheat, *Botrytis cinerea* (gray mold) on strawberries, vines, *Cercospora arachidicola* on groundnuts, *Pseudocercosporella herpotrichoides* on wheat, barley, *Pyricularia oryzae* on rice, *Phytophthora infestans* on potatoes and tomatoes, *Fusarium* and *Verticillium* species on various plants, *Plasmopara viticola* on vines, Alternaria species on vegetables and fruit.

The compounds I are applied by treating the fungi or the plants, seeds, materials or the soil to be protected from fungal attack with a fungicidally effective amount of the active compounds. They are applied before or after the infection of the materials, plants or seeds by the fungi.

They can be converted into the customary formulations, such as solutions, emulsions, suspensions, dusts, powders, pastes and granules. The application form depends on the particular intended use; they should in any case guarantee a fine and uniform dispersion of the naphthyl ether. The formulations are prepared in a known manner, eg. by extending the active compound with solvents and/or carriers, if desired using emulsifiers and dispersants, it also being possible to use other organic solvents as auxiliary solvents when water is used as a diluent. Suitable auxiliary substances for this purpose are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, argillaceous earths, talc, chalk) and ground synthetic minerals (eg. highly disperse silicic acid, silicates); emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

The fungicidal compositions in general contain from 0.1 to 95, preferably from 0.5 to 90, % by weight of active compound.

Depending on the type of effect desired, the application rates are from 0.02 to 3 kg of active compound per ha.

In seed treatment, active compound amounts of from 0.001 to 50 g, preferably 0.01 to 10 g, per kilogram of seed are in general needed.

The compositions according to the invention can also be present as fungicides together with other active compounds in the application form, eg. with herbicides, insecticides, growth regulators, fungicides or alternatively with fertilizers.

On mixing with fungicides, in many cases an increase in the fungicidal spectrum of action is obtained here.

The following list of fungicides with which the compounds according to the invention can be applied together should illustrate the combination possibilities, but not restrict them:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediamine bisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl) disulfide; nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropylcarbonate, diisopropyl 5-nitroisophthalate; heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino) phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazole carbamate, 2-methoxycarbonylaminobenzimidazole, 2-(fur-2-yl) benzimidazole, 2-(thiazol-4-yl)benzimidazole, N-(1,1, 2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfadiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine-1-oxide, 8-hydroxyquinoline or its copper salt, 2,3-dihydro-5-carboxanilido-6-methyl-1,4-oxathiin, 2,3-dihydro-5-carboxanilido-6-methyl-1,4-oxathiin-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(1-(2,2,2-trichloroethyl))formamide, 1-(3,4-dichloroanilino)-1-formyl-amino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol -1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and also various fungicides, such as dodecylguanidine acetate, 3-[3-(3,5-dimethyl-2-oxycyclohexyl)-2-hydroxyethyl] glutarimide, hexachlorobenzene, DL-methyl-N-(2,6-dimethylphenyl)- N-2-furoyl alaninate, DL-N-(2,6-dimethylphenyl)-N-(2'methoxyacetyl)alanine methyl ester, N-(2,6-dimethylphenyl)-N-chloroacetyl-D,L-2-aminobutyrolactone, DL-N-(2,6-dimethyl-phenyl)-N-(phenylacetyl)alanine methyl ester, 5-methyl-5-vinyl-3-(3,5-dichlorophenyl)-2,4-dioxo-1,3-oxazolidine, 3-[3,5-di-chlorophenyl-(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-ethylaminocarbonyl-2-methoximino]acetamide, 1-[2-(2,4-dichlorophenyl)pentyl]-1H-1,2,4-triazole, 2,4-difluoro-α-(1H-1,2,4-triazolyl-1-methyl) benzhydryl alcohol, N-(3-chloro- 2,6-dinitro-4-trifluoromethylphenyl)-5-trifluoromethyl-3-chloro-2-aminopyridine, 1-((bis(4-fluorophenyl)methylsilyl)methyl)- 1H-1,2,4-triazole.

The compounds of the formula I are additionally suitable to control pests from the class of insects, arachnida and nematodes effectively. They can be employed as pesticides in plant protection and in the hygiene, stored products protection and veterinary sectors.

The harmful insects include from the order of the butterflies (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera* bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.*

From the order of the dipterous insects (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia mortisans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterous insects (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the bed bugs (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the plant-sucking insects (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterous insects (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example, spiders (Acarina) such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root gall nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii,* stem and leaf eelworms, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active compounds can be applied as such or in the form of their formulations or the application forms prepared therefrom, eg. in the form of directly sprayable solutions, powders, suspensions or dispersions, emulsions, oil dispersions, pastes, dusts, scattering compositions or granules by spraying, atomizing, dusting, scattering or pouring. The application forms depend entirely on the purposes of use; they should in any case as far as possible guarantee the finest dispersion of the active compounds according to the invention.

The active compound concentrations in the ready-for-application preparations can be varied within substantial ranges.

In general, they are from 0.0001 to 10 %, preferably from 0.01 to 1%.

The active compounds can also be used with success in ultra-low volume processes (ULV), where it is possible to apply formulations containing more than 95 % by weight of active compound or even the active compound without additives.

The application rate of active compound for controlling pests under outdoor conditions is from 0.1 to 2.0, preferably from 0.2 to 1.0 kg/ha, depending on the control target.

For the preparation of directly sprayable solutions, emulsions, pastes or oil dispersions, mineral oil fractions of medium to high boiling point, such as kerosene or diesel oil, and also coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water are suitable. Aqueous application forms can be prepared from emulsion concentrates, pastes or wearable powders (oil dispersions) by addition of water. For the preparation of emulsions, pastes or oil dispersions, the substances can be homogenized in water as such or dissolved in an oil or solvent, by means of wetting agents, tackifiers, dispersants or emulsifiers. However, the concentrates consisting of active substance, wetting agent, tackifier, dispersant or emulsifier and possibly solvent or oil can also be prepared, which are suitable for dilution with water. Suitable surface-active substances are alkali metal, alkaline earth metal and ammonium salts of lignosulfonic acid, naphthalenesulfonic acid, phenolsulfonic acid, dibutylnaphthalenesulfonic acid, alkylarylsulfonates, alkylsulfates, alkylsulfonates, fatty alcohol sulfates and fatty acids and their alkali metal and alkaline earth metal salts, salts of sulfonated fatty alcohol glycol ethers, condensation products of sulfonated naphthalene and naphthalene derivatives with formaldehyde, condensation products of naphthalene or of naphthalenesulfonic acid with phenol and formaldehyde, polyoxyethylene octylphenol ether, ethoxylated isooctylphenol, octylphenol, nonylphenol, alkylphenol polyglycol ether, tributylphenyl polyglycol ether, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Powders, scattering compositions and dusts can be prepared by mixing or joint grinding of the active substances with a solid carrier.

The formulations in general contain from 0.01 to 95 % by weight, preferably from 0.1 to 90 % by weight, of the active compound. The active compounds are employed here in a purity of from 90 % to 100 %, preferably 95 % to 100 % (according to NMR spectrum).

Examples of formulations are:

I. 5 parts by weight of the compound No. 1.001 are intimately mixed with 95 parts by weight of finely divided Kaolin. A dust which contains 5 % by weight of the active compound is obtained in this way.

II. 30 parts by weight of the compound No. 1.003 are intimately mixed with a mixture of 92 parts by weight of powdered silica gel and 8 parts by weight of paraffin oil which has been sprayed onto the surface of this silica gel. A preparation of the active compound having good adhesion is obtained in this way (active compound content 23 % by weight).

III. 10 parts by weight of the compound No. 1.001 are dissolved in a mixture which consists of 90 parts by weight of xylene, 6 parts by weight of the addition product of 8 to 10 mol of ethylene oxide to 1 mol of oleic acid N-monoethanolamide, 2 parts by weight of calcium salt of dodecylbenzenesulfonic acid and 2 parts by weight of the addition product of 40 mol of ethylene oxide to 1 mol of castor oil (active compound content 9 % by weight).

IV. 20 parts by weight of the compound No. 1.002 are dissolved in a mixture which consists of 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16 % by weight).

V. 80 parts by weight of the compound No. 1.002 are well mixed with 3 parts by weight of the sodium salt of diisobutylnaphthalene-alpha-sulfonic acid, 10 parts by weight of the sodium salt of a lignosulfonic acid from a sulfite waste liquor and 7 parts by weight of powdered silica gel and the mixture is ground in a hammer mill (active compound content 80% by weight).

VI. 90 parts by weight of the compound No. 1.001 are mixed with 10 parts by weight of N-methyl-α-pyrrolidone and a solution is obtained which is suitable for application in the form of very small drops (active compound content 90 % by weight).

VII. 20 parts by weight of the compound No. 1.002 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02 % by weight of the active compound.

VIII. 20 parts by weight of the compound No. 1.003 are well mixed with 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray liquor is obtained which contains 0.1% by weight of the active compound.

Granules, eg. coated, impregnated and homogeneous granules, can be produced by binding the active compounds to solid carriers. Solid carriers are eg. mineral earths, such as silica gel, silicic acids, silicates, talc, kaolin, attapulgite, limestone, lime, chalk, bole, loess, clay, dolomite, diatomaceous earth, calcium sulfate and magnesium sulfate, magnesium oxide, ground synthetic materials, fertilizers, such as eg. ammonium sulfate, ammonium phosphate, ammonium nitrate, ureas and vegetable products, such as grain meal, tree bark, wood and nutshell meal, cellulose powder and other solid carriers.

Oils of various types, herbicides, fungicides, other pesticides and bactericides can be added to the active compounds, if appropriate also just immediately before application (tank-mix). These agents can be admixed to the compositions according to the invention in the weight ratio 1:10–10:1.

SYNTHESIS EXAMPLES

The procedures presented in the synthesis examples below are utilized with appropriate modification of the starting compounds to obtain further compounds I. The compounds thus obtained are shown in the following tables with physical data.

Preparation examples

1. Preparation of methyl 1-hydroxy-2-naphthylglyoxylates

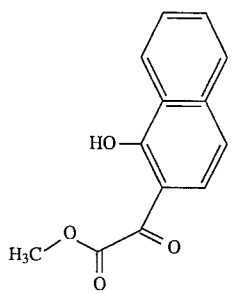

28.5 g (0.15 mol) of titanium tetrachloride are added at −10° C. under nitrogen to 150 ml of methylene chloride. First 22.3 g (0.15 mol) of 1-naphthol, dissolved in 100 ml of methylene chloride and subsequently 18.5 g (0.15 mol) of methyl oxalyl chloride are then added dropwise at −40° C. The mixture is stirred for a further 30 min at this temperature, some dilute hydrochloric acid is then added at room temperature (20° C.) and the mixture is poured onto ice. The organic phase is washed once with H₂O, dried over sodium sulfate and concentrated. 30 g (0.13 mol) of methyl 1-hydroxy-2-naphthylglyoxalate are obtained (87% yield).

¹H-NMR (CDCl₃): δ=4.05 (s, 3H), 7.25 (d, 1H), 7.40–7.80 (m, 4H), 8.45 (d, 1H), 13.00 ppm (s, 1H).

2. Preparation of methyl 2-hydroxy-2-naphthylglyoxylate O-methyl oxime

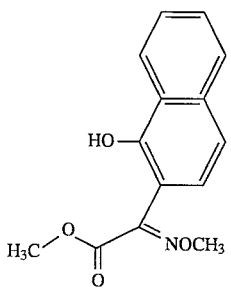

69 g (0.26 mol) of methyl 1-hydroxy-2-naphthylglyoxylate and 44 g (0.53 mol) of O-methylhydroxylamine hydrochloride are introduced into 800 ml of methanol and heated to reflux temperature for 6 h with stirring. The mixture is then concentrated, the residue is taken up in ethyl acetate, and the solution is washed with H₂O, dried over sodium sulfate and concentrated again. 52 g (0.20 mol) of methyl 1-hydroxy-2-naphthylglyoxylate O-methyl oxime are obtained (77% yield).

¹H-NMR (CDCl₃): δ=4.00(s,3H), 4.05(s,3H), 7.00(d, 1H), 7.30 (d, 1H), 7.40–7.90 (m, 4H), 8.35 (m, 1H), 10.90 ppm (s, 1H).

3. Preparation of methyl 1-[6-chloropyrimidin-4-yloxy]naphthyl-2-glyoxylate O-methyl oxime

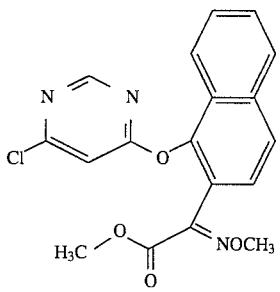

6 g (0.04 mol) of 4,6-dichloropyrimidine and 7 g (0.05 mol) of potassium carbonate are introduced into 60 ml of dimethylformamide. 7.7 g (0.03 mol) of the compound of Example 2 are added dropwise thereto at 0° C., and the mixture is stirred for 1 hour at 0° C. and then further overnight at RT. It is then poured onto ice and extracted with ether. The organic phase is washed with water, dried over sodium sulfate and concentrated. 8 g (72%) of product are obtained.

¹H-NMR (CDCl₃): δ=3.81 (s, 3H), 4.0 (s, 3H), 6.90 (s, 1H), 7.4–8.0 (m, 6H) and 8.50 ppm (s, 1H).

4. Preparation of methyl 1-[6-(2-cyanophenoxy)pyrimidin-4-yloxy]naphthyl-2-glyoxyalate O-methyl oxime 3.5 g (9 mmol) of the compound of Example 3 are stirred for 5 hours at 100° C. in 100 ml of DMF together with 1.2 g (10 mmol) of 2-cyanophenol, 1.4 g (10 mmol) of potassium carbonate and 100 mg of copper(I) chloride. The mixture is then poured onto ice and extracted with ether. The organic phase is washed with dilute sodium hydroxide solution, dried over sodium sulfate and concentrated. 3 g (73%) of product remain.

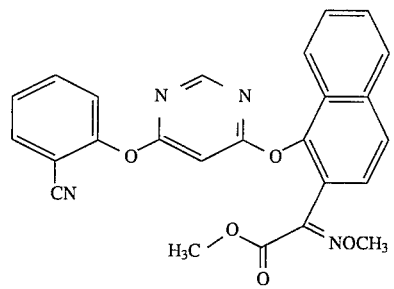

¹H-NMR (CDCl₃): δ=3.95(s,3H), 4.0(s,3H), 6.57(s, 1H), 7.22–8.0(m, 10H) and 8.3 ppm (s, 1H).

TABLE

I (n = 1)

| No. | X | Z | YR¹ | A | R² | phys. data [IR (cm⁻¹)] |
|---|---|---|---|---|---|---|
| 1.001 | O | NOCH₃ | OCH₃ | Pyrimidin-4,6-diyl | 2-CN—C₆H₄ | 1743, 1593, 1467, 1447, 1226, 1142, 1035 |

TABLE-continued

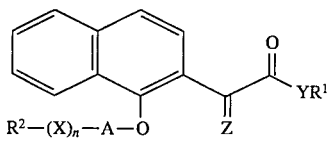

| No. | X | Z | YR$^1$ | A | R$^2$ | phys. data [IR (cm$^{-1}$)] |
|---|---|---|---|---|---|---|
| 1.002 | O | NOCH$_3$ | NHCH$_3$ | Pyrimidin-4,6-diyl | CH$_3$ | 1744, 1605, 1446, 1197, 1036, 814 |
| 1.003 | — | NOCH$_3$ | OCH$_3$ | Pyrimidin-4,6-diyl | Cl | 1731, 1557, 1449, 1360, 1347, 1231, 1084, 1033, 794 |

Examples of the biological action

Fungicidal activity

*Botrytis cinerea*

Paprika seedlings of the variety Neusiedler Ideal Elite having 4–5 well-developed leaves were sprayed with an aqueous active compound suspension until dripping wet. After the spray coating had dried on, the plants were sprayed with a conidia suspension of the fungus *Botrytis cinerea*. After 5 days at from 22° to 24° C. and high atmospheric humidity, the fungal attack on the leaves was assessed.

In this test the plants treated with 250 ppm of the compounds 1.001 and 1.003 showed an attack of 5%, while in the untreated plants 70% of the leaf surfaces were attacked.

*Erysiphe graminis* var. *tritici* (wheat mildew)

Wheat seedlings of the variety Frühgold were sprayed with an aqueous active compound suspension until dripping wet. After 24 h the plants were dusted with oidia (spores) of the fungus *Erysiphe graminis* var. *tritici* (wheat mildew). After 7 days at from 22° to 24° C. and from 75 to 80% atmospheric humidity the fungal attack on the leaves was assessed.

In this test the plants treated with 250 ppm of the compounds 1.001, 1.002 and 1.003 showed an attack of 15% and less, while in the untreated plants 65% of the leaf surfaces were attacked.

We claim:

1. A naphthyl ether of formula I (I)

wherein:

A is unsubstituted or substituted phenyl;

n is 1;

X is sulfur or nitrogen, the nitrogen atom carrying a radical selected from the group consisting of hydrogen, C$_1$–C$_4$-alkyl, C$_1$–C$_4$-alkoxy, C$_3$–C$_6$-cycloalkyl, unsubstituted phenyl, substituted phenyl, unsubstituted benzyl and substituted benzyl;

Y is nitrogen, the nitrogen atom carrying a radical selected from the group consisting of hydrogen, C$_1$–C$_4$-alkyl and C$_1$–C$_4$-alkoxy;

Z is CHOCH$_3$, NOCH$_3$, CHCH$_3$ or CHCH$_2$CH$_3$;

R$^1$ is C$_1$–C$_4$-alkyl;

R$^2$ is unsubstituted or substituted C$_1$–C$_6$-alkyl, C$_3$–C$_6$-cycloalkyl, C$_2$–C$_6$-alkenyl, C$_3$–C$_6$-alkynyl, unsubstituted or substituted phenyl.

2. The naphthyl ether of claim 1, wherein Z is NOCH$_3$.

3. The naphthyl ether of claim 1, wherein Z is CHOCH$_3$, CHCH$_3$ or CHCH$_2$CH$_3$.

4. The naphthyl ether of claim 1, wherein R$^2$ is unsubstituted or substituted phenyl.

5. The naphthyl ether of claim 1, wherein R$^2$ is unsubstituted or substituted phenyl.

6. The naphthyl ether of claim 1, wherein X is sulfur.

7. The naphthyl ether of claim 1, wherein X is nitrogen, the nitrogen atom carrying a radical selected from the group consisting of hydrogen, C$_1$–C$_4$-alkyl, C$_1$–C$_4$-alkoxy, C$_3$–C$_6$-cycloalkyl, unsubstituted phenyl, substituted phenyl, unsubstituted benzyl and substituted benzyl.

8. The naphthyl ether of claim 1, wherein R$^2$ is phenyl substituted with 1–5 halogen atoms or 1–3 radicals selected from the group consisting of: amino, carboxyl, carbonylamino, formyl, formylamino, hydroxyl, isocyano, nitro, sulfoxyl, thiocarboxamido, thiocyanato, alkyl, haloalkyl, alkylcarbonyl, alkylcarbonyloxy, alkylcarbonylthio, alkylcarbonylamino, alkylsulfonyl, alkylsulfonyloxy, alkylsulfonylamino, alkoxy, haloalkoxy, alkoxycarbonyl, alkoxyiminoalkyl, alkylthio, alkylthiocarbonyl, alkylamino, alkylaminocarbonyl, dialkylamino, dialkylaminocarbonyl, cycloalkyl, cycloalkoxy, cycloalkylthio, cycloalkylamino, alkenyl, alkenyloxy, alkynyl, alkynyloxy, phenylsulfonyl, phenylsulfonyloxy, and phenylsulfonylamino.

9. A composition against animal pests or harmful fungi, containing an effective amount of the naphthyl ether of claim 1 and a suitable solvent or carrier.

10. The composition of claim 9, wherein said animal pests are insects, Arachnida or nematodes.

11. A process for controlling animal pests or harmful fungi, comprising treating the pests or harmful fungi, their environment or the plants, surfaces, materials or spaces to be kept free from said pests or fungi with an effective amount of the naphthyl ether of claim 1.

* * * * *